US007288565B2

(12) United States Patent
Kanie et al.

(10) Patent No.: US 7,288,565 B2
(45) Date of Patent: Oct. 30, 2007

(54) AZASUGAR COMPOUND

(75) Inventors: Osamu Kanie, Tokyo (JP); Chikako Saotome, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 331 days.

(21) Appl. No.: 10/726,550

(22) Filed: Dec. 4, 2003

(65) Prior Publication Data

US 2004/0147591 A1 Jul. 29, 2004

Related U.S. Application Data

(63) Continuation-in-part of application No. PCT/JP02/05672, filed on Jun. 7, 2002.

(30) Foreign Application Priority Data

Jun. 8, 2001 (JP) ............................. 2001-173855

(51) Int. Cl.
*A61K 31/40* (2006.01)
*C07D 207/04* (2006.01)
(52) U.S. Cl. ...................... 514/425; 548/541; 514/424
(58) Field of Classification Search ................ 548/541; 514/424, 425
See application file for complete search history.

(56) References Cited

U.S. PATENT DOCUMENTS

| 5,348,954 A |   | 9/1994 | Almen et al. |
| 5,451,679 A | * | 9/1995 | Barta et al. .................. 546/219 |
| 5,663,342 A | * | 9/1997 | Barta et al. ..................... 546/6 |

FOREIGN PATENT DOCUMENTS

| JP | 4-502619 | 5/1992 |
| WO | 95/24392 | 9/1995 |
| WO | 00/68194 | 11/2000 |
| WO | 03/008379 | 1/2003 |

OTHER PUBLICATIONS

Wrodnigg et al (1997): STN International HCAPLUS database, Columbus (OH), accession No. 1997: 530913.*
Barta et al (1995): STN International HCAPLUS database, Columbus (OH), accession No. 1995: 994843.*
T. M. Wordnigg et al., "Novel, Lipophilic Derivatives of 2,5-dideoxy-2,5-imino-D-mannitol (DMDP) are Powerful; β-Glucosidase Inhibitors," Bioorganic and Medicinal Chemistry Letters, vol. 11, No. 8, pp. 1063-1064, 2001.
A. Hermetter et al., "Powerful Probes for Glycosidases: Novel, Fluorescently Tagged Glycosidase Inhibitors," Bioorganic and Medicinal Chemistry Letters, vol. 11, No. 10, pp 1339-1342, 2001.
T. M. Wordnigg et al., "Biologically Active 1-aminodeoxy and 1-o-alkyl Derivatives of the Powerful D-glucosidase Inhibitor 2,5-dideoxy-2,5-imino-D-mannitol," Journal of Carbohydrate Chemistry, vol. 19, No. 8, pp. 975-990, 2000.
I. McCort et al., "Synthesis and Evaluation as Glycosidase Inhibitors of 2,5-imino-D-glucitol and 1,5-Imino-D-mannitol Related Derivatives," Bioorganic and Medicinal Chemistry, vol. 8, No. 1, pp. 135-143, 2000.
C. H. Wong et al, "Synthesis and Evaluation of Homoazasugars as Glycosidase Inhibitors," Journal of Organic Chemistry, vol. 60, No. 6, 1492-1501, 1995.
R. C. Reynolds et al., "Ethambutol-sugar Hybrids as Potential Inhibitors of Mycobacterial Cell-wall Biosynthesis," Carbohydrate Research, vol. 317, pp. 164-179, 1999.
I. McCort et al., "Synthesis of Ester- and Amide-Linked Pseudo-azadisaccharides via Coupling of D-glucose with 6-amino-6-deoxy-2,5-imino-D-glucitol," Tetrahedron Letters, vol. 39, No. 25, pp. 4463-3366, 1998.

(Continued)

*Primary Examiner*—Golam M. M. Shameem
(74) *Attorney, Agent, or Firm*—Greenblum & Bernstein, P.L.C.

(57) ABSTRACT

The present invention provides a compound represented by the formula (I) or a salt thereof:

$$\text{(I)}$$

wherein $R^1$ represents a hydrogen atom, a $C_{1-10}$ alkyl group optionally having a substituent, or a protecting group of N; $R^2$ represents a $C_{1-10}$ alkyl group optionally having a substituent or a $C_{2-10}$ alkenyl group optionally having a substituent; $R^3$ and $R^4$ independently represent a hydrogen atom or a protecting group of hydroxyl group; X represents —N($R^5$)$R^6$ or a residue of amino acid or of an amino group of a peptide wherein $R^5$ and $R^6$ independently represent a hydrogen atom, a $C_{1-10}$ alkyl group optionally having a substituent, or a $C_{3-12}$ cycloalkyl group optionally having a substituent; and Y represents a hydrogen atom, —$CH_2NH_2$, —$CONH_2$, or —COOH. The compound of the present invention is useful as a specific inhibitor of sugar chain related enzymes such as glycosyltransferase and glycosidase, and is useful as, for example, a medicine for treating or preventing diseases associated with sugar chain related enzymes.

17 Claims, 7 Drawing Sheets

OTHER PUBLICATIONS

K. D. Janda et al., "Chemical Selection for catalysis in Combinatorial Antibody Libraries," Science, vol. 275, No. 5302, pp. 945-948, 1997.

S. H. Kang et al., "Intramolecular Cyclization of $C_2$ Symmetric and *meso*-Iodo Amino Alcohols: A Synthetic Approach to Azasugars," Tetrahedron Letters, vol. 38, No. 4, pp. 607-610, 1997.

I. McCort et al., "Practical Route to D-Manno and D-Gluco Azasugars from $C_2$ Symmetric Bis-aziridines," Tetrahedron Letters, vol. 37, No. 43, pp. 7717-7720, 1996.

L. Campanini et al., "One Step Synthesis of Sulfur and Nitrogen Linked Aza-disaccharide Precursors from D-Mannitol Derived Bis-aziridines," Tetrahedron Letters, vol. 37, No. 29, pp. 5095-5098, 1996.

L. Campanini et al., "Concise Synthesis of New Homoazasugars. Fully Substituted, Functionally Diverse Pyrrolidines," Tetrahedron Letters, vol. 36, No. 44, pp. 8015-8018, 1995.

J. Fitremann et al., "Regioselective Cyanide Ring Opening of $C_2$ Symmetric Bis-Aziridines by Cyanide," Synlett, vol. 3, pp. 235-237, 1995.

M. H. M. G. Schumacher-Wandersleb et al., "Preparation of the N-Acetylglucosaminidase Inhibitor 1-Acetamido-1,2,5-trideoxy-2,5-imino-D-glucitol from Methyl α-D-Mannopyranoside," Liebigs Ann. Chem., vol. 6, pp. 555-561, 1994.

J. Fitremann et al., "2,5-Disubstituted Pyrrolidines from D-Mannitol-Derived Bis-Aziridines," Tetrahedron Letters, vol. 36, No. 8, pp. 1201-1204, 1994.

R. Kornfeld et all., Ann. Rev. Biochem., vol. 54, pp. 631-634, 1985.

I. Brockhausen, Biochimica et Biophysica Acta, vol. 1473, pp. 67-95, 1999.

T.D. Butters et al., Chem. Rev., vol. 100, pp. 4683-4696, 2000.

M. Sinnott et al., Chem. Rev., vol. 90, pp. 1171-1202, 1990.

C.S. Rye et al., Curr. Opin. Chem. Biol., vol. 4, pp. 573-580, 2000.

U.M. Unligil et al., Curr. Opin. Struct. Biol., vol. 10, pp. 510-517, 2000.

B. Winchester et al., Biochem. J., vol. 290, pp. 743-749, 1993.

G.W.J. Fleet et al., Tetrahedron Lett., vol. 26, pp. 3127-3130, 1985.

K.K.-C. Liu et al., J. Org. Chem., vol. 56, pp. 6280-6289, 1991.

A. Kato et al., Carbohydr. Res., vol. 316, pp. 95-103, 1999.

M. Takebayashi et al., J. Org. Chem., vol. 64, pp. 5280-5291, 1999.

C. Saotome et al., Bioorg. Med. Chem., vol. 8, pp. 2249-2261, 2000.

T. Kajimoto et al., J. Am. Chem. Soc., vol. 113, pp. 6187-6196, 1991.

Y. Ichikawa et al., J. Am. Chem. Soc., vol. 120, pp. 3007-3018, 1998.

G. Legler et al., Carbohydr. Res., vol. 155, pp. 119-129, 1986.

C.H. Wong et al., Angew. Chem. Int. Ed. Engl., vol. 34, pp. 412-432, 1995.

C.H. Wong et al., Angew. Chem. Int. Ed. Engl., Vol. 34, 521-546, 1995.

A.B. Hughes et al., Nat. Prod. Rep., pp. 135-162, 1994.

X. Qian et al., Glycotransferase Inhibitors, in Carbohydrates in Chemistry and Biology, B. Ernst et al. ed., vol. 3, pp. 293-312.

M. Takayanagi et al., J. Org. Chem., Vol. 65, pp. 3811-3815, 2000.

U.J. Nilsson et al. Bioorg. Med. Chem., vol. 6, pp. 1563-1575, 1998.

R. Wischnat et al., Bioorg. Med. Chem. Lett., vol. 8, pp. 3353-3358, 1998.

A. Lohse et al., Bioorg. Med. Chem., vol. 7, pp. 1965-1971, 1999.

A. Lohse et al., Tetrahedron Lett., vol. 40, pp. 3033-3036, 1999.

C. Malet, Carbohydrate Research, vol. 303, pp. 51-65, 1997.

* cited by examiner galactose analogue    mannose analogue

A

B

C

D

E

F

G

A

B

AZASUGAR COMPOUND

This is a continuation-in-part of International Application No. PCT/JP02/05672, with an international filing date of Jun. 7, 2002, which claims priority of Japanese Application No. 2001-173855, filed on Jun. 8, 2001, both of which are incorporated by reference herein in their entireties.

TECHNICAL FIELD

The present invention relates to a novel azasugar compound and more particularly to an azasugar compound having an activity of inhibiting sugar chain related enzymes. The present invention also relates to a medicine using the aforementioned azasugar compound.

BACKGROUND ART

Sugar chain related enzymes (oligosaccharide-processing enzymes) such as glycosyltransferase and glycosidase are important classes of molecules involved in the synthesizing specific oligosaccharide structures on proteins (Kornfeld, R. et al. (1985), Ann. Rev. Biochem. 54, 631-664; and Brockhausen, I. et al. (1999), Biochim. Biophys. Acta 1473, 67-95) and sphingolipids (Butters, T. D. et al. (2000), Chem. Rev. 100. 4683-4696). The use of specific inhibitors of these enzymes enables the regulation of cellular functions, and thus these inhibitors are of interest. Enzymatic hydrolysis of a glycosidic bond generally takes place via general acid and base catalysts that require two critical residues (i.e., a proton donor and a nucleophile) (Sinnott, M. L. et al. (1990), Chem. Rev. 90, 1171-1202; Rye, C. S. et al. (2000), Curr. Opin. Chem. Biol. 4, 573-580; and Unligil, U. M. et al. (2000), Curr. Opin. Struct. Biol. 10, 510-517). A distorted half-chair-like transition state leading to a carboxonium ion is considered to be involved in the reaction (FIG. 1). Five-membered iminocyclitols carrying hydroxyl groups with specific orientation to mimic the shape and charge of the transition state of the reacting sugar moiety have been shown to be potent inhibitors of such enzymes (Winchester, B. et al. (1993), Biochem. J. 290, 743-749; Fleet, G. W. J. et al. (1985), Tetrahedron Lett. 26, 3127-3130; Liu, K. K.-C. et al. (1991), J. Org. Chem. 56, 6280-6289; Kato, A. et al. (1999), Carbohydr. Res. 316-95-103; Takebayashi, M. et al. (1999), J. Org. Chem. 64, 5280-5291; and Saotome, C. et al. (2000), Bioorg. Med. Chem. 8, 2249-2261). Since a cation-like transition state is expected to be involved in both the glycosyltransferase and glycosidase catalyzed reaction, five- and six-membered iminocyclitols can be used as core components for the development of transition-state analog inhibitors of both families of enzymes (Winchester, B. et al. (1993), Biochem. J. 290, 743-749; Fleet, G. W. J. et al. (1985), Tetrahedron Lett. 26, 3127-3130; Liu, K. K.-C. et al. (1991), J. Org. Chem. 56, 6280-6289; Kato, A. et al. (1999), Carbohydr. Res. 316-95-103; Takebayashi, M. et al. (1999), J. Org. Chem. 64, 5280-5291; Saotome, C. et al. (2000), Bioorg. Med. Chem. 8, 2249-2261; Kajimoto, T. et al. (1991), J. Am. Chem. Soc. 113, 6187-6196; Ichikawa, Y. et al. (1998), J. Am. Chem. Soc. 120, 3007-3018; Legler, G. et al. (1986), Carobydr. Res. 155, 119-129; Wong, C.-H. et al. (1995), Angew. Chem. Int. Ed. Engl. 34, 412-432; Wong, C.-H. et al. (1995), Angew. Chem. Int. Ed. Engl. 34, 521-546; Hughes, A. B. et al. (1994), Nat. Prod. Rep. 135-162; and Qian, X. et al. (2000), Glycosyltransferase inhibitors, In Carbohydrates in Chemistry and Biology, (Ernst, B., Hart, G. W. & Sinay, P., ed.) vol. 3, pp. 293-312, Wiley-VCH, Weinheim).

DISCLOSURE OF THE INVENTION

An object of the present invention is to provide a compound having a specific inhibitory activity against sugar chain related enzymes such as glycosyltransferase and glycosidase. Another object of the present invention is to provide a medicine utilizing the aforementioned specific inhibitors against the sugar chain related enzymes.

The inventors of the present invention have conducted concentrated studies in order to attain the above objects. As a result, they have synthesized a series of five-membered iminocyclitols, and have shown that some of them possess strong and interesting inhibitory activities against glycosyltransferases and glycosidases (Takebayashi, M. et al. (1999), J. Org. Chem. 64, 5280-5291; and Saotome, C. et al. (2000), Bioorg. Med. Chem. 8, 2249-2261). Since a rational design and synthesis to afford desired inhibitory is difficult due to the limited information regarding the structure of active site, the inventors of the present invention have examined whether or not a compound that would exhibit desirable inhibitory activity could be screened by a method using a combinatorial library derived from 5-membered iminocyclitol. The inventors of the present invention at first created a library with small diversity, and then evaluated whether or not the contents thereof would become inhibitors of sugar chain related enzymes. More specifically, a group of compounds that are members of 5-membered iminocyclitol were synthesized, and the inhibitory activities thereof on various forms of glycosyl hydrolase and glycosyltransferase were evaluated. Thus, the present invention has been completed.

Thus, the present invention provides a compound represented by the formula (I) or a salt thereof:

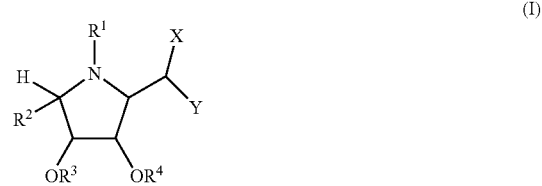

(I)

wherein $R^1$ represents a hydrogen atom, a $C_{1-10}$ alkyl group optionally having a substituent, or a protecting group of N; $R^2$ represents a $C_{1-10}$ alkyl group optionally having a substituent or a $C_{2-10}$ alkenyl group optionally having a substituent; $R^3$ and $R^4$ independently represent a hydrogen atom or a protecting group of hydroxyl group; X represents $-N(R^5)R^6$ or a residue of amino acid or of an amino group of a peptide wherein $R^5$ and $R^6$ independently represent a hydrogen atom, a $C_{1-10}$ alkyl group optionally having a substituent, or a $C_{3-12}$ cycloalkyl group optionally having a substituent; and Y represents a hydrogen atom, $-CH_2NH_2$, $-CONH_2$, or $-COOH$.

Preferably, the configuration of the compound represented by the formula (I) is represented by the following formula (Ia):

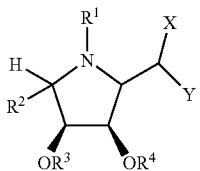

(Ia)

wherein $R^1$, $R^2$, $R^3$, $R^4$, X, and Y are as defined above.

More preferably, the configuration of the compound represented by the formula (I) is represented by the following formula (Ib):

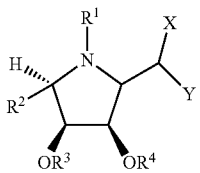

(Ib)

wherein $R^1$, $R^2$, $R^3$, $R^4$, X, and Y are as defined above.

Particularly preferably, the configuration of the compound represented by the formula (I) is represented by the following formula (Ic):

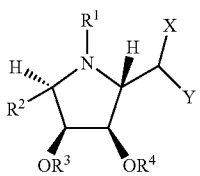

(Ic)

wherein $R^1$, $R^2$, $R^3$, $R^4$, X, and Y are as defined above.

Preferably, $R^2$ represents —$CH_2OR^{12}$ wherein $R^{12}$ represents a hydrogen atom or a protecting group of hydroxyl group.

Another aspect of the present invention provides an inhibitor of sugar chain related enzymes which comprises a compound represented by the formula (I) or a salt thereof, and a medicine which comprises, as an active ingredient, the compound represented by the formula (I) or a salt thereof. The medicine of the present invention can be used as, for example, a medicine for the therapy or prevention of diseases associated with sugar chain related enzymes. More specifically, it can be used as an antiviral agent, an anticancer agent, or an immunostimulant agent.

Further aspects of the present invention provide a method for inhibiting sugar chain related enzymes which comprises administrating a pharmaceutically effective amount of a compound represented by the formula (I) or a salt thereof to mammalians including humans, and a method for treating or preventing diseases associated with sugar chain related enzymes which comprises administering a pharmaceutically effective amount of a compound represented by the formula (I) or a salt thereof to mammalians including humans.

Further aspects of the present invention provide the use of a compound represented by the formula (I) or a salt thereof in the production of an inhibitor of sugar chain related enzymes, and the use of a compound represented by the formula (I) or a salt thereof in the production of a medicine (specifically, a medicine for the therapy or prevention of diseases associated with sugar chain related enzymes, such as an antiviral agent, an anticancer agent, or an immunostimulant agent).

A further aspect of the present invention provides a method for producing a compound represented by the formula (I) which comprises a step of reacting a compound represented by the formula (II):

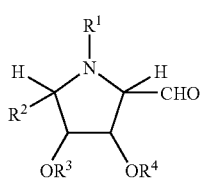

(II)

wherein $R^1$ represents a hydrogen atom, a $C_{1-10}$ alkyl group optionally having a substituent, or a protecting group of N; $R^2$ represents a $C_{1-10}$ alkyl group optionally having a substituent or a $C_{2-10}$ alkenyl optionally having a substituent; and $R^3$ and $R^4$ independently represent a hydrogen atom or a protecting group of hydroxyl group; with a compound represented by the formula X—H:

wherein X represents —$N(R^5)R^6$ or a residue of amino acid or of an amino group of a peptide, and $R^5$ and $R^6$ independently represent a hydrogen atom, a $C_{10}$ alkyl group optionally having a substituent, or a $C_{3-12}$ cycloalkyl group optionally having a substituent;

in the presence of a reducing agent, to produce a compound represented by the formula (III):

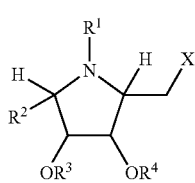

(III)

wherein $R^1$, $R^2$, $R^3$, $R^4$ and X are as defined above.

A further aspect of the present invention provides a method for producing a compound represented by the formula (I) which comprises a step of reacting a compound represented by the formula (II):

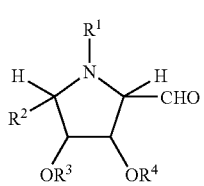

(II)

wherein $R^1$ represents a hydrogen atom, a $C_{1-10}$ alkyl group optionally having a substituent, or a protecting group of N;

R² represents a $C_{1-10}$ alkyl group optionally having a substituent or a $C_{2-10}$ alkenyl optionally having a substituent; and R³ and R⁴ independently represent a hydrogen atom or a protecting group of hydroxyl group;

with a compound represented by the formula X—H:

wherein X represents —N(R⁵)R⁶ or a residue of amino acid or of an amino group of a peptide, and R⁵ and R⁶ independently represent a hydrogen atom, a $C_{1-10}$ alkyl group optionally having a substituent, or a $C_{3-12}$ cycloalkyl group optionally having a substituent;

and a cyanation agent in the presence of Lewis acid, to produce a compound represented by the formula (IV):

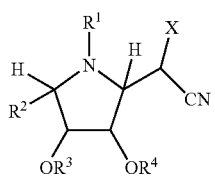

(IV)

wherein R¹, R², R³, R⁴ and X are as defined above.

A: inhibition of α-Glc-ase at the inhibitor concentration of $1×10^{-4}$M;

B: inhibition of α-Man-ase at the inhibitor concentration of $1×10^{-5}$M;

C: inhibition of α-Gal-ase at the inhibitor concentration of $1×10^{-5}$M;

D: inhibition of α-GalNAc-ase at the inhibitor concentration of $1×10^{-7}$M;

E and F: inhibition of β-Gal-ase at the inhibitor concentration of $1×10^{-3}$M and $1×10^{-5}$ respectively; and G: inhibition of β-1,4-GalT-ase at the inhibitor concentration of $5×10^{-4}$M Synthesis of compounds 1 and 8 is reported in Saotome, C. et al. (2000), Bioorg. Med. Chem. 8, 2249-2261.

Figure 7:
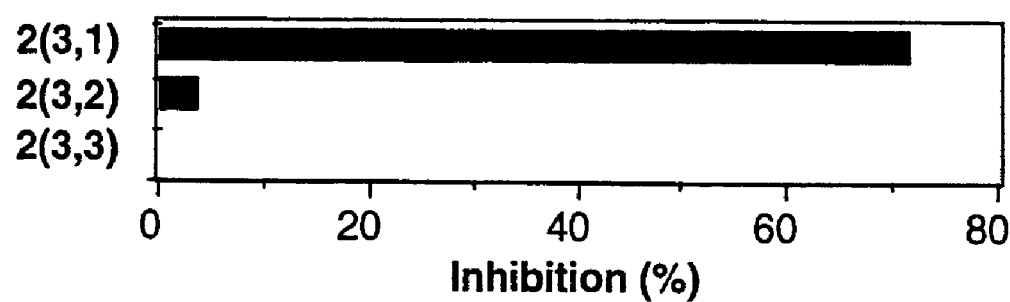
Figure 7:
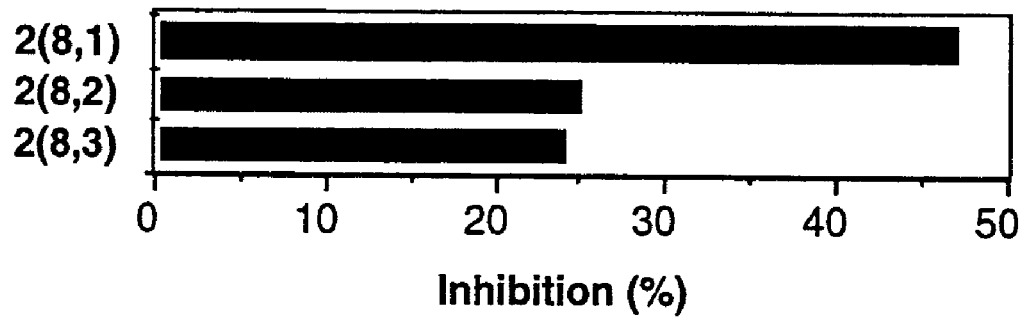

FIG. 7 shows inhibitory activities of compound 2 (3, Y) and compound 2 (8, Y) against α-Man-ase and α-GalNAc-ase. Two types of compound 2 (3, Y) and compound 2 (8, Y) were selected, and the effect of group Y was evaluated:

A: inhibition of α-Man-ase at the inhibitor concentration of $1×10{-}-5$M; and

B: inhibition of α-GalNAc-ase at the inhibitor concentration of $1×10^{-7}$M.

BEST MODE FOR CARRYING OUR THE INVENTION

Embodiments of the practice of the present invention are hereinafter described in detail.

In this description, $C_{1-10}$ alkyl group may be an alkyl group of 1 to 10 carbon atoms, having for example, straight-chain, branched, cyclic, or a combined form thereof. Specific examples thereof include methyl, ethyl, propyl, isopropyl, butyl, isobutyl, tert-butyl, cyclopropylmethyl, pentyl, and hexyl.

In this description, $C_{2-10}$ alkenyl may be an alkenyl group of 2 to 10 carbon atoms, having for example, straight-chain, branched, cyclic, or a combined form thereof. Specific examples thereof are groups wherein at least one carbon-carbon bond in the aforementioned alkyl is a double bond, such as allyl, butenyl, or octenyl.

In this description, examples of $C_{3-12}$ cycloalkyl include cyclopropyl, cyclobutyl, cyclopentyl, cyclohexyl, and adamantyl.

The aforementioned alkyl, alkenyl or cycloalkyl may have one or more substituents if necessary. Such substituents are not particularly limited, and examples thereof include hydroxyl, oxo (═O), a halogen atom (any of a fluorine, chlorine, bromine, or iodine atom), lower alkoxyl (such as methoxy, ethoxy, or n-propoxy), substituted or unsubstituted aryloxy (such as phenoxy), amino, monoalkylamino (such as methylamino or ethylamino), dialkylamino (such as dimethylamino, diethylamino, or ethylmethylamino), mercapto, alkylthio (such as methylthio or ethylthio), amidino, guanidino, ureido, carboxyl, alkoxycarbonyl, aryl (such as substituted or unsubstituted phenyl), cycloalkyl (such as cyclopropyl, cyclobutyl, cyclopentyl, cyclohexyl, or adamantyl), and heterocycle. Specific examples of heterocycle used herein include 3- to 10-membered saturated or unsaturated heterocycles containing at least one N, O, or S atom. They may be monocyclic or may form a condensed ring with another ring. Specific examples of heterocycle include, but are not limited to, tetrahydrofuran, pyrrolidine, piperidine, piperazine, morpholine, thiophene, furan, pyrrole, imidazole, pyrazole, pyridine, pyrimidine, pyrazine, pyridazine, triazole, triazine, indole, indazole, purine, thiadiazole, oxadiazole, quinoline, phthalazine, naphthylidine, quinoxaline, quinazoline, cinnoline, pteridine, acridine, phenanthroline, phenazine, tetrazole, thiazole, oxazole, benzimidazole, benzoxazole, benzthiazole, benzoselenazole, indolenine, and tetrazaindene.

Preferable substituents for imparting enzyme specificity or enhancing enzyme affinity among the aforementioned substituents include those that hydrophobically interact or form hydrogen bonds with amino acid side chains in the vicinity of the active site of the enzyme or those that interact between charges thereof as a substituent of X or R² in the formula above, and a certain type of aglycon as an entire body thereof such as nucleic acid base or amino acid. A substituent (Y) having different electronic absorption affects the locality of the electron of an imino group in the pyrrolidine ring and adjusts the inhibitory activity.

The protecting groups of N used herein are not particularly limited, and persons skilled in the art can select adequate examples thereof. Specific examples of protecting groups of N are listed below, but are not limited thereto:

t-butoxycarbonyl, methylcarbonyl, 9-fluorenylmethylcarbonyl, 2,2,2-trichloroethylcarbonyl, 2-trimethylsilylethylcarbonyl, vinylcarbonyl, allylcarbonyl, benzyloxycarbonyl, toluenesulfonyl, benzenesulfonyl, trichloromethylsulfonyl, and the aforementioned groups with its terminus being bound to a resin.

The protecting groups of hydroxyl group used herein are not particularly limited, and persons skilled in the art can select adequate examples thereof. Specific examples of protecting groups of hydroxyl group are listed below, but are not limited thereto:

(Ether Type)

methyl, methoxymethyl, methylthiomethyl, benzyloxymethyl, t-butoxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 4-methoxytetrahydropyranyl, 4-methoxytetrahydrothiopyranyl, 4-methoxytetrahydrothiopyranyl S,S-dioxide, tetrahydrofuranyl, and tetrahydrothiofuranyl;

1-ethoxyethyl, 1-methyl-1-methoxyethyl, 1-(isopropoxy) ethyl, 2,2,2-trichloroethyl, 2-(phenylselenyl)ethyl, t-butyl, allyl, cinnamyl, p-chlorophenyl, benzyl, p-methoxybenzyl, o-nitrobenzyl, p-nitrobenzyl, p-halobenzyl, p-cyanobenzyl, 3-methyl-2-picolyl N-oxide, diphenylmethyl, 5-dibenzosuberyl, triphenylmethyl, α-naphthyldiphenylmethyl, p-methoxyphenyldiphenylmethyl, p-(p'-bromophenacyloxy)phenyldiphenylmethyl, 9-anthryl, 9-(9-phenyl)xanthenyl, 9-(9-phenyl-10-oxo)anthryl, benzisothiazolyl S,S-dioxide; and trimethylsilyl, triethylsilyl, isopropyldimethylsilyl, t-butyldimethylsilyl (TMDMS), (triphenylmethyl)dimethylsilyl, t-butyldiphenylsilyl, methyldiisopropylsilyl, methyl di-t-butylsilyl, tribenzylsilyl, tri-p-xylylsilyl, triisopropylsilyl, and triphenylsilyl;

(Ester Type)

formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, p-P-phenylacetate, 3-phenylpropionate, 3-benzoylpropionate, isobutyrate, monosuccinoate, 4-oxopentanoate, pivaloate, adamantoate, crotonate, 4-methoxycrotonate, (E)-2-methyl-2-butenoate, benzoate, o-(dibromomethyl)benzoate, o-(methoxycarbonyl)benzoate, p-phenylbenzoate, 2,4,6-trimethylbenzoate, p-P-benzoate, and α-naphthoate;

(Carbonate Type)

methyl carbonate, ethyl carbonate, 2,2,2-trichloroethyl carbonate, isobutyl carbonate, vinyl carbonate, allyl carbonate, cinnamyl carbonate, p-nitrophenyl carbonate, benzyl carbonate, p-methoxybenzyl carbonate, 3,4-dimethoxybenzyl carbonate, o-nitrobenzyl carbonate, p-nitrobenzyl carbonate, and S-benzyl thiocarbonate; and (Others)

N-phenylcarbamate, N-imidazolylcarbamate, borate, nitrate, N,N,N',N'-tetramethylphosphorodiamidate, and 2,4-dinitrophenyl-sulfenate.

Methods for introducing or deprotecting the aforementioned protecting groups are known to persons skilled in the art and are described in, for example, Teodora, W. Green, Protective Groups in Organic Synthesis, John Wiley & Sons, Inc. (1981).

In the present invention, X represents —N($R^5$)$R^6$ or a residue of amino acid or of an amino group of peptide.

Types of amino acid used herein are not particularly limited, and may be a naturally occurring amino acid residue, a non-naturally occurring amino acid residue, or a derivative thereof. Specifically, amino acid may be L-amino acid, D-amino acid, or a mixture thereof. The amino acid may be α-amino acid, β-amino acid, γ-amino acid, or δ-amino acid, and naturally occurring α-amino acid is preferable. The term "non-naturally occurring amino acid" used herein refers to all amino acids except for 20 types of naturally occurring amino acids that constitute naturally occurring proteins, which are glycine, L-alanine, L-valine, L-leucine, L-isoleucine, L-serine, L-threonine, L-aspartic acid, L-glutamic acid, L-asparagin, L-glutamine, L-lysine, L-arginine, L-cystine, L-methionine, L-phenylalanine, L-tyrosine, L-tryptophan, L-histidine, and L-proline. Specific examples thereof include: (1) non-naturally occurring amino acid obtained by substituting an atom in a naturally occurring amino acid with another substance; (2) an optical isomer of side chain of a naturally occurring amino acid; (3) non-naturally occurring amino acid obtained by introducing a substituent to a side chain of a naturally occurring amino acid; and (4) non-naturally occurring amino acid obtained by substituting a side chain of a naturally occurring amino acid with another substance to modify hydrophobicity, reactivity, a charge state, molecular size, capability of forming hydrogen bonds, or the like.

The "peptide" used herein is comprised of several amino acids joined together by peptide bonds. The length thereof is not particularly limited, and is generally 2 to 20 amino acid residues, preferably 2 to 10 amino acid residues, and more preferably 2 to 5 amino acid residues.

In the aforementioned compounds according to the present invention, $R^1$ is preferably a hydrogen atom, $R^2$ is preferably —$CH_2OH$, $R^3$ and $R^4$ are each independently preferably hydrogen atoms. X is preferably butylamino, 2,2-N,N-dimethylethylamino, dodecylamino, ethanolamino (2-hydroxyethylamino), adamantanamino, methoxypropylamino(3-methoxypropylamino), tetrahydrofurfurylamino, phenethylamino, or cyclohexylamino, and Y is preferably a hydrogen atom, aminomethyl, or carboxomide. Further, X is most preferably dodecylamino or phenethylamino, and Y is most preferably a hydrogen atom.

The compound represented by the formula (I) may be present in the form of salt, depending on the type of substituent. A physiologically acceptable salt of the compound represented by the formula (I) can be used in the medicine of the present invention.

Types of the salts are not particularly limited, and examples thereof include acid addition salts, metal salts, ammonium salts, or organic amine addition salts. The acid addition salts include inorganic acid salts such as hydrochloride, sulfic acid, nitric acid or phosphate, and organic acid salts such as acetate, maleate, fumarate, or citrate. The metal salts include alkali metal salts such as sodium salt or potassium salt, alkaline earth metal salts such as magnesium salt or calcium salt, aluminum salts, or zinc salts. The ammonium salts include salts of ammonium or tetramethylammonium. The organic amine addition salts include morpholine or piperidine addition salts.

The compound represented by the formula (I) include isomers such as a positional isomer, geometrical isomer, tautomer, stereoisomer (including a conformational isomer), or optical isomer. A mixture comprising any possible isomers and a mixture comprising arbitrary amounts of two or more of these isomers can be used in the medicine of the present invention. Specific examples of the stereoisomer of the compound represented by the formula (I) are shown in the formulae (Ia), (Ib) and (Ic) herein. It is described in Takebayashi, M. et al., J. Org. Chem., 1999, 64, 5280-5291 that, in research on pyrrolidine compounds having different diol configurations, two types of stereoisomers at the aforementioned site were synthesized, and a group of (R)-compounds were found to exhibit better activity of inhibiting a D-configuration of sugar chain related hydrolytic enzyme as compared with the steric (S)-compound.

When it is intended to obtain a salt of the compound represented by the formula (I) and when the compound represented by the formula (I) is obtained in the form of salt, it may be purified in that state. When the compound is obtained in a free form, it may be dissolved or suspended in an adequate solvent, and a salt is formed with the addition of acid or base, and then the salt may be isolated and purified.

The compound represented by the formula (I) or a salt thereof may be present in the form of an addition product with water or with one of a variety of solvents (a hydrate or solvate). These addition products can be used in the medicine of the present invention.

Any crystal form of the compound represented by the formula (I) or a salt thereof can be used in the medicine of the present invention.

The method for producing the compound represented by the formula (I) is then described. As shown in Scheme 1 in the Examples below, the compound represented by the formula (I) can be synthesized from aldehyde form 3 by any of the following two types of processes. Compounds 2, 3, 4, and 5 mentioned below are identical to the compounds shown in Scheme 1.

Aldehyde compound 3 used as a starting material in the present invention is a known compound, and it can be synthesized by a method described in Saotome, C. et al. (2000), Bioorg. Med. Chem. 8, 2249-2261. In the case where $R^1$ is a $C_{1-10}$ alkyl group optionally having a substituent and $R^2$ is a $C_{10}$ alkyl group optionally having various substituents or a $C_{2-10}$ alkenyl group optionally having various substituents in the formula (I), an adequate starting material can be selected, and a technology of functional group conversion reaction which is known to persons skilled in the art can be employed. Thus, aldehyde compound 3 having a desired substituent can be synthesized in accordance with the method described in Saotome, C. et al. (2000), Bioorg. Med. Chem. 8, 2249-2261.

The first method is a method for producing a compound represented by the formula (I) (including the formulae (Ia), (Ib), and (Ic), and the same applies hereinafter), wherein Y is a hydrogen atom. At first, compound 3 is subjected to reductive amination to produce compound 4, and a protecting group is then deprotected if necessary. Thus, compound 2 which corresponds to a compound represented by the formula (I) wherein Y is a hydrogen atom, can be synthesized.

A reaction wherein compound 3 or a stereoisomer thereof is subjected to reductive amination to produce compound 4 can be carried out by, for example, adding an amine compound (an amino acid or peptide can also be used as this amine compound) represented by the formula X—H to a solution of compound 3 in an adequate inert solvent (such as toluene), stirring the mixture, and adding a solution of a reducing agent in an adequate inert solvent (such as THF). The reaction temperature is not particularly limited as long as the reaction proceeds. The reaction can be generally carried out at about 0° C. to 50° C., and preferably at room temperature. The reaction period is not particularly limited, and the reaction can be carried out for several hours to several days. The reducing agent that can be used herein is a reagent which selectively reduces imine without reducing aldehyde. A specific example thereof is $NaBH_3CN$. The reaction mixture after the reaction can be subjected to post-treatments such as washing and drying by conventional techniques, and can be then used for deprotection reaction if necessary. The deprotection reaction can be suitably selected depending on the type of protecting group.

The second method is a method for producing a compound represented by the formula (I) wherein Y is —$CH_2NH_2$ or —$CONH_2$. At first, compound 3 is subjected to the Strecker reaction to produce compound 5, and a nitrile group is then converted to an amino or amide group. Thus, compound 2, which corresponds to a compound represented by the formula (I) wherein Y is —$CH_2NH_2$ or —$CONH_2$, can be synthesized.

A reaction wherein compound 3 is subjected to the Strecker reaction to produce compound 5 can be carried out by, for example, adding an amine compound (an amino acid or peptide may also be used as this amine compound) represented by a formula X—H to a solution of aldehyde compound 3 in an adequate inert solvent (such as toluene), stirring the mixture, and adding a cyanation agent and Lewis acid. The reaction temperature is not particularly limited as long as the reaction proceeds. The reaction can be generally carried out at about 0° C. to 50° C., and preferably at room temperature. The reaction period is not particularly limited, and the reaction can be carried out for several hours to several days.

Examples of cyanation agents that can be used herein include TMSCN (TMS cyanide) and HCN (hydrocyanic acid).

Examples of a Lewis acid that can be used herein include zinc trichloride, aluminum trichloride, boron trifluoride, tin tetrachloride, titanium tetrachloride, and ytterbium triflate.

The reaction mixture after the reaction can be subjected to post-treatments such as washing and drying by conventional techniques, and can be then used for subsequent reactions.

Compound 5 that was obtained by the above Strecker reaction is then subjected to either one of the following two types of reactions. Thus, compound 2, which corresponds to a compound represented by the formula (I) wherein Y is —$CH_2NH_2$ or —$CONH_2$, can be obtained.

In order to produce a compound represented by the formula (I) wherein Y is —$CH_2NH_2$, a nitrile group in compound 5 may be converted to an amino group. This reaction can be carried out by, for example, dissolving compound 5 in methanol and hydrochloric acid, adding Pd(OH)$_2$ on carbon, and stirring the mixture in an $H_2$ atmosphere. The reaction temperature is not particularly limited as long as the reaction proceeds. The reaction can be generally carried out at about 0° C. to 50° C., and preferably at room temperature. The reaction period is not particularly limited, and the reaction can be carried out for several hours to several days. The obtained reaction mixture is subjected to post-treatment and purification by conventional techniques. Thus, compound 2, which corresponds to a compound represented by the formula (I) wherein Y is —$CH_2NH_2$, can be obtained.

In order to produce a compound represented by the formula (I) wherein Y is —$CONH_2$, a nitrile group in compound 5 may be converted to an amide group. This reaction can be carried out by, for example, dissolving compound 5 in methanol and KOH, adding hydrogen peroxide, and stirring the mixture. The obtained reaction mixture is extracted, dried and dissolved in methanol and HCl solution again. $Pd(OH)_2$ on carbon is then added thereto. A compound of interest can be produced by stirring the reaction mixture in an $H_2$ atmosphere. The reaction temperature is not particularly limited as long as the reaction proceeds. The reaction can be generally carried out at about 0° C. to 50° C., and preferably at room temperature. The reaction period is not particularly limited, and the reaction can be carried out for several hours to several days. The obtained reaction mixture is subjected to post-treatment and purification by conventional techniques. Thus, compound 2, which corresponds to a compound represented by the formula (I) wherein Y is —$CONH_2$, can be obtained.

In order to produce a compound represented by the formula (I) wherein Y is —COOH, a nitrile group in compound 5 may be hydrolyzed to convert it to a carboxyl group. Specifically, compound 5 is dissolved in hydrochloric acid and dioxane, and the resultant is refluxed. Thus, a compound represented by the formula (I) wherein Y is —COOH can be produced. The reaction period is not particularly limited, and the reaction can be carried out for several tens of minutes to several days.

The present invention further relates to an inhibitor of sugar chain related enzymes which comprises the compound represented by the formula (I) (including general formulae (Ia), (Ib), and (Ic), and the same applies hereinafter) or a salt thereof, and a medicine which comprises the compound represented by the formula (I) or a salt thereof (they are generically referred to as the "medicine of the present invention" herein).

The medicine of the present invention is useful for treating or preventing diseases associated with sugar chain related enzymes. For example, it can be used as an antiviral agent, an anticancer agent, or an immunostimulant agent.

When the compound of the present invention is used as an inhibitor of sugar chain related enzymes, examples of target sugar chain related enzymes include glycolytic enzymes (such as glycohydrolase) and glycosyltransferase.

When the medicine of the present invention is used as an antiviral agent, the type of the target viral disease is not particularly limited. Diseases caused by virus infections include, for example, Japanese encephalitis, dengue fever, measles, epidemic parotitis, epidemic roseola, influenza, hepatitis A, hepatitis B, hepatitis C, yellow fever, hemorrhagic fever, meningitis, infantile diarrhea, rabies, Ebola hemorrhagic fever, Lassa fever, polio, St. Louis encephalitis, adult T cell leukemia, and AIDS. Examples of known intractable diseases that are deduced to be caused by virus infections include chronic rheumatism, systemic erythematodes, multiple sclerosis, subacute sclerosing panencephalitis, Alzheimer's disease, ulcerative colitis, Crohn's disease, Kawasaki disease, and diabetes. The antiviral agent of the present invention is useful for treating or preventing these diseases.

When the medicine of the present invention is used as an anticancer agent, a type of target tumor or cancer is not particularly limited. Examples thereof include all malignant and benign tumors, and includes carcinomas (epithelial malignant tumors), sarcomas (non-epithelial malignant tumors), and mixed types thereof.

The type of cancer can be classified based on the site that it developed in Specific examples of cancers include hypophyseal adenoma, neuroglioma, acoustic neuroma, brain tumor, pharyngeal cancer, laryngeal cancer, thymoma, mesothelioma, breast cancer, lung cancer, gastric cancer, esophageal cancer, colon cancer, hepatocellular cancer, pancreatic cancer, pancreatic endocrine tumor, cholangiocarcinoma, gallbladder cancer, penile cancer, ureteral cancer, renal cell carcinoma, orchioncus (testicular tumor), prostate cancer, bladder cancer, vulvar cancer, uterine cancer, uterine sarcoma, vaginal cancer, ovarian cancer, ovarian germ cell tumor, malignant melanoma, mycosis fungoides, skin cancer, soft part sarcoma, malignant lymphoma, non Hodgkin's lymphoma, myelodysplastic syndromes, multiple myeloma, plasma cell tumor, and brown lymphoma. The aforementioned examples represent examples of the cancers, and the cancers are not limited thereto.

The compound of the present invention was found to inhibit an inactivator ($\alpha$-GalNAc-ase) of a macrophage activator, and thus is useful as an immunostimulant agent. The examples of cases where the medicine of the present invention is used as an immunostimulant agent include a case where various diseases that are considered to be caused by the lowered immunocompetence of an organism due to infections, stress and the like are prevented. Specifically, the medicine of the present invention can be used for the purpose of the protection of an organism from pathogenic bacteria or virus infections and the prevention of cancer.

The medicine of the present invention can comprise, as an active ingredient, one or two or more substance selected from the group consisting of a compound represented by the formula (I), a physiologically acceptable salt thereof, a hydrate thereof, and a solvate thereof. Any mixed isomers or a pure isomer may be used.

The medicine of the present invention is preferably provided in the form of a pharmaceutical composition comprising one or two or more pharmaceutically acceptable additive and the aforementioned substance which is an active ingredient.

The medicine of the present invention can be administered orally or parenterally (such as intravenous, intramuscular, hypodermic, or endodermic injection, intrarectal administration, or transmucosal administration). Examples of pharmaceutical compositions that are suitable for oral administration include tablets, granules, capsules, powders, solutions, suspensions, and syrups. Examples of pharmaceutical compositions that are suitable for parenteral administration include injections, drops, suppositories, and transdermal absorbents. The dosage forms of the medicine of the present invention are not limited thereto.

Types of the pharmaceutical additives that are used for producing the medicine of the present invention are not particularly limited, and persons skilled in the art can select adequate one. Examples of the pharmaceutical additives that can be used include excipients, disintegrators or disintegration assistants, binders, lubricants, coating agents, bases, solubilizers or solubilization assistants, dispersants, suspensions, emulsifiers, buffers, antioxidants, preservatives, isotonizing agents, pH regulators, solubilizers, and stabilizers. The specific ingredients of the pharmaceutical additives used for these purposes are well known to persons skilled in the art.

Examples of pharmaceutical additives that can be used for producing preparations for oral administration include: excipients such as glucose, lactose, D-mannitol, starch, or crystalline cellulose; disintegrators or disintegration assistants such as carboxymethyl cellulose, starch, or carboxy methylcellulose calcium; binders such as hydroxypropyl cellulose, hydroxypropyl methylcellulose, polyvinylpyrrolidone, or gelatin; lubricants such as magnesium stearate or talc; coating agents such as hydroxypropyl methylcellulose, sucrose, polyethylene glycol, or titanium oxide; and bases such as vaseline, liquid paraffin, polyethylene glycol, gelatin, kaolin, glycerin, purified water, or hard fat.

Examples of pharmaceutical additives that can be used for producing injection or drop preparations include: solubilizers or solubilization assistants that can constitute aqueous injections or injections to be dissolved before use, such as distilled water for injection, physiological saline, or propylene glycol; isotonizing agents such as glucose, sodium chloride, D-mannitol, or glycerin; and pH regulators such as inorganic acids, organic acids, inorganic bases, or organic bases.

The medicine of the present invention can be administered to mammalians, including humans.

The dosage of the medicine of the present invention should be appropriately increased or decreased in accordance with conditions such as the age, sex, weight, and the medical condition of the patient, and the route of administration. The amount of active ingredient is generally about 1 µg/kg to 1,000 mg/kg, and preferably about 10 µg/kg to 100 mg/kg, per day per adult. The aforementioned dosage of medicine can be administered in a single dose or in several separate doses (for example, about 2 to 4 times) per day.

All of the contents disclosed in the description of Japanese Patent Application No. 2001-173855, which is a priority document of the present application, are incorporated herein by reference in their entirety The present invention is described in detail with reference to the following examples, but the present invention is not limited to these examples.

EXAMPLES (A) Materials and Methods (1) Materials

Following enzymes were purchased as indicated below: Saccaromyces. Sp.-derived α-glucosidase (α-Glc-ase; α-glucoside glucohydrolase; EC 3.2.1.20) (ToYoBo); Jack Bean-derived α-mannosidase (α-Man-ase; α-D-mannoside mannohydrolase; EC 3.2.1.24) (Sigma); Green Coffee Bean-derived α-galactosidase (α-Gal-ase; α-D-galactoside galactohydrolase; EC 3.2.1.22) (Sigma); *Aspergillus oryzae*-derived 62-galactosidase (β-Gal-ase; β-D-galactoside galactohydrolase; EC 3.2.1.23) (Sigma); Chicken Liver-derived α-GalNAc-ase (2-acetamido-2-deoxy-α-D-galactoside acetamidodeoxygalactohydrolase; EC 3.2.1.49) (Sigma); Bovine Milk-derived 13-1,4-galactosyltransferase (13-1,4-GalT-ase; EC 2.4.1.22) (Sigma); and pig-derived *E. coli* recombinant α-1,3-galactosyltransferase (α-1,3-GalT-ase; EC 2.4.1.90) (Carbiochem).

4-Methyl umbelliferyl 2-acetamido-2-deoxy-β-D-glucopyranoside (4-MU-GlcNAc) was purchased from Wako Pure Chemical Ltd. UDP galactose and 5'-diphosphonate (UDP) were purchased from Sigma. Cacodylic acid sodium salt, HEPES [2-{4-(2-hydroxyethyl)-1-piperazinyl}ethanesulfonic acid], MES [2-(N-morpholino) ethanesulfonic acid], $MnCl_2$, sodium tetraborate, and potassium hydroxide were purchased from Nacalai Tesque Inc. Double deionized water was prepared by a Mili-Q system (Millipore Corp.). Sep-Pak cartridges were purchased from Waters Corp. Millex-GS syringe filter (0.22 mm×4 mm, i.d.) was purchased from Nihon Millipore Ltd.

(2) General Methods for Chemical Synthesis

Dried solvents were used for all reactions. Solutions were evaporated under reduced pressure at a bath temperature not exceeding 50° C. Column chromatography was performed on silica gel (Merck Kieselgel 60) or Iatro Beads (60 µl, Dia-latron Laboratories). Gel permeation chromatography was performed using Bio Gel P-2. TLC spots were visualized using 7%12 molybdo(VI)phosphoric acid n-hydrate in ethanol. JEOL EX-270 spectrometer was used to obtain NMR spectra at 25° C.

$^1$H NMR (270 MHz) was recorded in $CDCl_3$ or $D_2O$ using $Me_4Si$ (d 0.00) or DOH (d 4.80) as the internal standard. $^{13}C$ NMR (67.5 MHz) was recorded in $CDCl_3$ or $D_2O$ using $Me_4Si$ (d 0.0), $CDCl_3$ (d 77.0), or $CD_3CN$ (d 118.2) as the internal standard. Only partial assignments were reported. MALDITOF mass spectra were recorded on Voyager (Applied BioSystems) with 2,5-dihydroxybenzoic acid as matrix. Color development of TLC was determined using ATTO Densitograph software library Lane Analyzer (ATTO Corp.).

(3) General Methods for Glycosyltransfer Reactions and Analysis

Enzyme reactions were performed in a total volume of 250 µl in microtubes. Reaction mixture contained 0.1 M cacodylate buffer (pH 7), 10 mM $MnCl_2$, 0.1 mM UDP-Gal, 0.2 mM 4-MU-glycoside, 0.5 mM inhibitor, and 20 mU/mL galactosyltransferase. After incubation for 5 minutes at 37° C., the reaction was terminated by the addition of 50 µl of 0.1M boric acid heating at 80° C. for 10 minutes. The mixture was filtered with Millex GV Filter to remove the precipitate.

Kinetic analysis was performed on a Waters Quanta 4000E capillary electrophoresis system, which was equipped with a fused silica capillary of i.d. 75 µm. Samples were loaded by means of hydrostatic pressure at 10 cm higher for 10 seconds. Detection was carried out by on-column measurement of UV absorption at 214 nm at 7.5 cm from the cathode. Pherograms were recorded on Millennium 2010 System (Waters Corp.).

(4) Typical Procedure for Reductive Amination of Compound 3

Phenethylamine (4.4 µl, 0.035 mmol) was added to a solution of aldehyde 3 (9 mg, 0.017 mmol) in toluene (3001 µl) at 0° C., the mixture was stirred at room temperature for 2 hours. Then, 1M solution of $NaBH_3CN$ in THF (51.0 µl, 3 equivalent amounts) was added thereto at 0° C., and the mixture was stirred at room temperature overnight. The mixture was diluted with ethyl acetate, washed with saturated $NaHCO_3$, and dried over $MgSO_4$. Conversion yields of reductive amination were estimated by densitographic analysis of TLC. The spots were visualized by molybdophosphate reagent. Only UV-positive spots corresponding to the protected iminocyclitol were analyzed.

Yields (%): 4 (1), 98.1; 4 (2), 42.4; 4 (3), 80.3; 4 (4). 57.5; 4 (5), 80.9; 4 (6), 61.0; 4 (7), 54.9; 4 (8), 79.4; 4 (9), 80.3.

After removal of the solvent, the residue was dissolved in methanol (0.8 ml) and 1M HCl (0.2 ml), and the solution was stirred with a catalytic amount of 20% $Pd(OH)_2$ under $H_2$ atmosphere at room temperature for 2 days. The crude material obtained after removal of the catalyst and solvent, was dissolved in $H_2O$ (1 ml), and the solution was stirred with Dowex 1X8 (OH form) at room temperature for 30 minutes. After filtration and removal of the solvent, the residue was dissolved in H$_2$O, and the solution was applied onto a Waters Sep-Pak Plus CM cartridge, which was pretreated with 1M HCl (10 ml) and water (20 ml). The cartridge was washed with H$_2$O (20 ml), where after elution with 10% NH$_3$ (10 ml), filtration through a Millex GV Filter, and lyophilization gave compound 2 (8, 1) (2.5 mg, 53% from compound 3). In the parallel reaction, compounds 2 (1,1) (55%), 2 (2,1) (65%), 2 (3,1) (10%), 2 (4,1) (80%), 2 (5,1) (36%), 2 (6,1) (74%), 2 (7,1) (63%), and 2 (9,1) (29%) were obtained. Selected physical data of these compounds are listed below.

2 (1,1); $^1$H-NMR (D$_2$O): δ 4.20 (t, 1H, J=3.8 Hz), 3.98 (dd, 1H, J=4.0, 8.4 Hz), 3.84 (dd, 1H, J=6.6, 11.2 Hz), 3.69 (dd, 1H, J=4.7, 11.2 Hz), 3.34 (dd, 1H, J=3.5, 6.6 Hz), 0.96 (t, 3H, J=7.3 Hz, CH$_3$); MALDI-TOF MS Calcd. for C$_{10}$H$_{22}$N$_2$O$_3$: 218; Found: m/z 219 (M+H)$^+$.

2 (2,1); $^1$H-NMR (D$_2$O): δ 4.19 (t, 1H, J=3.9 Hz), 3.91 (dd, 1H, J=4.4, 8.6 Hz), 3.84 (dd, 1H, J=6.5, 10.9 Hz), 3.67 (dd, 1H, J=6.6, 11.2 Hz), 2.66 (s, 6H, N(CH$_3$)$_2$).

2 (3,1); $^1$H-NMR (D$_2$O): δ 4.19 (t, 1H, J=3.5 Hz), 3.97 (dd, 1H, J=3.9, 7.8 Hz), 0.89 (t, 3H, J=6.7 Hz, CH$_3$); MALDI-TOF MS Calcd. for C$_{16}$H$_{34}$N$_2$O$_3$: 302; Found: m/z 303 (M+H)$^+$.

2 (4,1); $^1$H-NMR (D$_2$O): δ 4.19 (t, 1H, J=3.8 Hz), 3.96 (dd, 1H, J=4.3, 8.5 Hz); MALDI-TOF MS Calcd. For C$_8$H$_{18}$N$_2$O$_4$: 206; Found: m/z 207 (M+H)$^+$.

2 (5,1); $^1$H-NMR (D$_2$O): δ 4.30 (t, 1H, J=3.5 Hz), 4.19 (dd, 1H, J=3.5, 8.6 Hz); MALDI-TOF MS Calcd. For C$_{16}$H$_{28}$N$_2$O$_3$: 296; Found: m/z 297 (M+H)$^+$.

2 (6,1); $^1$H-NMR (D$_2$O): δ 4.19 (t, 1H, J=3.8 Hz), 3.94 (dd, 1H, J=4.2, 8.3 Hz), 3.82 (dd, 1H, J=6.8, 11.3 Hz), 3.67 (dd, 1H, J=6.2, 11.3 Hz), 3.58 (t, 2H, J=6.3 Hz), 3.38 (s, 3H, OCH$_3$), 2.93 (dd, 1H, J=4.7, 12.2 Hz), 2.81 (t, 2H, J=7.2 Hz), 1.85 (quinter, 2H, J=6.8 Hz); MALDI-TOF MS Calcd. For C$_{10}$H$_{22}$N$_2$O$_4$: 234: Found: m/z 235 (M+H)$^+$.

2 (7,1); $^1$H-NMR (D$_2$O): δ 4.24 (t, 1H, J=3.6 Hz), 4.19 (t, 1H, J=3.7 Hz), 4.03 (dd, 1H, J=4.1, 8.6 Hz); MALDI-TOF MS Calcd. For C$_{11}$H$_{22}$N$_2$O$_4$: 246; Found: m/z 247 (M+H)$^+$.

2 (8,1); $^1$H-NMR (D$_2$O): δ 7.43-7.35 (m, 5H), 4.16 (t, 1H, J=4.0 Hz), 3.90 (dd, 1H, J=3.9, 8.2 Hz), 3.80 (dd, 1H, J=6.9, 11.1 Hz); MALDI-TOF MS Calcd. For C$_{14}$H$_{22}$N$_2$O$_3$: 266; Found: m/z 267 (M+H)$^+$.

2 (9,1); $^1$H-NMR (D$_2$O): δ 4.18 (t, 1H, J=3.4 Hz), 3.96 (dd, 1H, J=4.4, 8.3 Hz), 3.82 (dd, 1H, J=6.6, 10.8 Hz), 3.67 (dd, 1H, J=6.6, 10.5 Hz); MALDI-TOF MS Calcd. For C$_{12}$H$_{24}$N$_2$O$_3$: 244; Found: m/z 245 (M+H)$^+$.

(5) Typical Procedure for Strecker Reaction of Compound 3

To a solution of aldehyde 3 (24 mg, 0.045 mmol) in toluene (700 μl), phenethylamine (6.9 μl, 0.054 mmol) was added at 0° C., and the mixture was stirred at room temperature for 2 hours. Then, TMSCN (18.1 μl, 0.14 mmol) and 0.5M solution of zinc chloride in THF (9.0 μl, 0.1 equivalent amount) was added at 0° C., and the mixture was stirred at room temperature for overnight. The mixture was diluted with ethyl acetate, washed with saturated NaHCO$_3$, and dried over MgSO$_4$. After removal of the solvent, the crude material of nitrile compound 5 (8) (29 mg, 96.0% p (6:4)) was obtained, where % p stands for purity of the product in the crude mixture as estimated by densitographic analysis of TLC, and the following number in parentheses indicates the ration of diastereoisomers. Of those without the ratio indicate that the stereoisomers had same Rf values. Spots were visualized by molybdophosphate reagent. Only the UV-positive spots corresponding to protected iminocyclitol were analyzed. In parallel reaction, compound 5 (1) (43 mg, 81.9% p (1:1), from compound 3 (39 mg, 0.074 mmol)), compound 5 (2) (26 mg, 58.2% p, from compound 3 (27 mg, 0.052 mmol)), compound 5 (3) (27 mg, 91.2% p (6:4), from compound 3 (28 mg, 0.053 mmol)), compound 5 (4) (29 mg, 67.8% p, from compound 3 (27 mg, 0.051 mmol)), compound 5 (5) (30 mg, 70.6% p, from compound 3 (24 mg, 0.046 mmol)), compound 5 (6) (27 mg, 56.9% p (6:4), from compound 3 (25 mg, 0.046 mmol)), compound 5 (7) (26 mg, 87.5% p (6:4), from compound 3 (26 mg, 0.048 mmol)), and compound 5 (9) (30 mg, 57.0% p, from compound 3 (26 mg, 0.050 mmol)) were obtained. These compounds were used for the next reaction without purification. Selected physical data are shown below.

5(1); $^1$H-NMR (CDCl$_3$): δ 3.62 (d, 1H, J=8.4 Hz, CHCN), 1.43 (s, 9H, C(CH$_3$)$_3$), 0.91 (t, 3H, J=7.0 Hz, CH$_3$); $^{13}$C-NMR (CDCl$_3$); 119.35 and 118.65 (CN), 80.99 (C(CH$_3$)$_3$), 28.29 (C(CH$_3$)$_3$), 13.84 (CH$_3$); MALDI-TOF MS Calcd. for C$_{37}$H$_{47}$N$_3$O$_5$: 613; Found: m/z 614 (M+H)$^+$.

5(2); $^1$H-NMR (CDCl$_3$): δ 3.63 (d, 1H, J=9.0 Hz, CHCN), 2.22 (s, 6H), 1.44 (s, 9H); MALDI-TOF MS Calcd. for C$_{37}$H$_{48}$N$_4$O$_5$: 628; Found: m/z 629 (M+H)$^+$.

5(3); $^1$H-NMR (CDCl$_3$): δ 4.12 (t, 1H, J=8.5 Hz), 3.63 (d, 1H, J=8.5 Hz, CHCN), 1.43 (s, 9H), 0.88 (t, 3H, J=6.4 Hz); MALDI-TOF MS Calcd. for C$_{43}$H$_{59}$N$_3$O$_5$: 697; Found m/z 698 (M+H)$^+$, 720 (M+Na)$^+$, 736 (M+K)$^+$.

5(4); $^1$H-NMR (CDCl$_3$): δ 1.44 (s, 9H); MALDI-TOF MS Calcd. for C$_{35}$H$_{43}$N$_3$O$_6$: 601; Found: m/z 602 (M+H)$^+$, 624 (M+Na)$^+$.

5(5); $^1$H-NMR (CDCl$_3$): δ 3.64 (d, 1H, J=8.1 Hz, CHCN), 1.46 (s, 9H): MALDI-TOF MS Calcd. for C$_{43}$H$_{53}$N$_3$O$_5$: 691; Found: m/z 692 (M+H)$^+$.

5(6); $^1$H-NMR (CDCl$_3$): δ 3.63 (d, 1H, J=8.3 Hz, CHCN), 3.31 (s, 3H), 1.44 (s, 9H).

5(7); $^1$H-NMR (CDCl$_3$): δ 3.63 (d, 1H, J=7.5 Hz, CHCN), 1.43 (s, 9H); MALDI-TOF MS Calcd. for C$_{38}$H$_{47}$N$_3$O$_6$: 641; Found: m/z 642 (M+H)$^+$.

5 (8); $^1$H-NMR (CDCl$_3$): δ 4.26 (dt. J=2.5, 7.0 Hz, 1H), 3.94 (d, 2H, J=4.1 Hz), 3.61 (t, 1H, J=6.5 Hz), 1.44 (s, 9H); $^{13}$C-NMR (CDCl$_3$); 118.58 (CN), 81.00 (C(CH$_3$)$_3$), 28.14 (C(CH$_3$)$_3$); MALDI-TOF MS Calcd. for C$_{41}$H$_{47}$N$_3$O$_5$: 661; Found: m/z 662 (M+H)$^+$.

5(9); $^1$H-NMR (CDCl$_3$): δ 4.14 (t, 1H, J=8.3 Hz), 3.98 (d, 2H, J=4.8 Hz0, 3.63 (d, 1H, J=6.6 Hz, CHCN), 1.45 (s, 9H): MALDI-TOF MS Calcd. for C$_{39}$H$_{49}$N$_3$O$_5$: 639; Found m/z 640 (M+H)$^+$.

(6) Typical Transformation Reaction of Nitrile to Amino Group: Synthesis of Compound 2 (8, 2)

To a solution of crude compound 5(8) (8 mg, corresponding to compound 2 (7 mg, 0.013 mmol)) dissolved in methanol (0.8 ml) and 1M HC$_1$ (0.2 ml) was added a catalytic amount of 20% Pd(OH)$_2$ on carbon. The reaction mixture was stirred under H$_2$ atmosphere at room temperature for 4 days. The crude material, obtained after removal of the catalyst and solvent, was dissolved in H$_2$O (1 ml), and the solution was stirred with Dowex 1X8 (OH form) at room temperature for 30 minutes. After filtration and removal of the solvent, the residue was dissolved in H$_2$O, and the solution was applied onto a Waters Sep-Pak Plus CM cartridge which was pretreated with 1M HCl (10 ml) and water (20 ml). The cartridge was washed with H$_2$O (20 ml), where after elution with 10% NH$_3$ (10 ml), filtration through a Millex GV Filter, and lyophilization gave compound 2 (8, 2) (2.3 mg, 58% from compound 3). In parallel reaction, compounds 2 (1,2) (51%), 2 (2,2) (41%), 2 (3,2) (8%), 2 (4,2) (41%), 2 (5,2) (32%), 2 (6,2) (31%), 2 (7,2) (27%), and 2 (9,2) (12%) were obtained. Selected physical data are listed below.

2 (1,2); $^1$H-NMR (D$_2$O): δ 0.90 (t, 3H, J=6.5 Hz, CH$_3$).

2 (2,2); $^1$H-NMR (D$_2$O): δ 1.95 (s, 6H);

2 (3,2); MALDI-TOF MS Calcd. for C$_{17}$H$_{37}$N$_3$O$_5$: 331; Found: m/z 332 (M+H)$^+$.

2 (4,2); $^1$H-NMR (D$_2$O): δ 3.75 (t, J=5.6 Hz), 3.00 (t, J=5.6 Hz); MALDI-TOF MS Calcd. for C$_9$H$_{21}$N$_3$O$_4$: 235; Found: m/z 236 (M+H)$^+$, 274 (M+K)$^+$.

2 (5,2); MALDI-TOF MS Calcd. For C$_{17}$H$_{31}$N$_3$O$_3$: 325; Found: m/z 326 (M+H).

2 (8,2); MALDI-TOF MS Calcd. for C$_{15}$H$_{25}$N$_3$O$_3$: 295; Found: m/z 296 (M+H)$^+$.

2 (9,2); MALDI-TOF MS Calcd. for C$_{13}$H$_{27}$N$_3$O$_3$: 273; Found: m/z 274 (M+H)$^+$, 312 (M+K)$^+$.

(7) Typical Transformation Reaction of Nitrile to Amide Group: Synthesis of Compound 2 (1, 3)

To a solution of crude compound 5 (1) (8 mg, corresponding to compound 3 (10 mg, 0.018 mmol)) in methanol (0.8 ml) and 6M KOH (0.2 ml) was added 30% H$_2$O$_2$ (17 μl, 0.15 mmol). The reaction mixture was stirred at 50° C. for 2 hours. After cooling, the reaction mixture was poured to ice-water and extracted with CH$_2$Cl$_2$, and dried over MgSO$_4$. To this residue dissolved in methanol (0.8 ml) and 1M HCl (0.2 ml) was added a catalytic amount of 20% Pd(OH)$_2$ on carbon. The reaction mixture was stirred under H$_2$ atmosphere at room temperature for 3 days. The crude material, obtained after removal of the catalyst and solvent, was dissolved in H$_2$O (1 ml), and the solution was stirred with Dowex 1X8 (OH form) at room temperature for 30 minutes. After filtration and removal of the solvent, the residue was dissolved in H$_2$O, and the solution was applied onto a Waters Sep-Pak Plus CM cartridge which was pretreated with 1M HCl (10 ml) and water (20 ml). The cartridge was washed with H$_2$O (20 ml), where after elution with 10% NH$_3$ (10 ml), filtration through a Millex GV Filter, and lyophilization gave compound 2 (1, 3) (1.4 mg, 28% from compound 3). In parallel reaction, compounds 2 (2,3) (42%), 2 (3,3) (15%), 2 (4,3) (33%), 2 (5,3) (17%), 2 (6,3) (28%), 2 (7,3) (12%), 2 (8,3) (27%), and 2 (9,3) (26%) were obtained. Selected physical data are listed below.

2 (1,3); $^1$H-NMR (D$_2$O): δ 3.34 (t, J=6.5 Hz), 0.92 (t, J=6.2 Hz); MALDI-TOF MS Calcd. for C$_{11}$H$_{23}$N$_3$O$_4$: 261; Found: m/z 262 (M+H)$^+$; Before hydrogenolysis; MALDI-TOF MS Calcd. for C$_{37}$H$_{49}$N$_3$O$_6$: 631; Found: m/z 632 (M+H)$^+$.

2 (2,3); MALDI-TOF MS Calcd. for C$_{11}$H$_{24}$N$_4$O$_4$: 276; Found: m/z 277 (M+H)$^+$; Before hydrogenolysis: MALDI-TOF MS Calcd. for C$_{37}$H$_{50}$N$_4$O$_6$: 646; Found: m/z 647 (M+H)$^+$, 685 (M+K)$^+$.

2 (3,3); $^1$H-NMR (D$_2$O): δ 0.89 (t, 3H, J=6.0 Hz); MALDI-TOF MS Calcd. for C$_{17}$H$_{35}$N$_3$O$_4$: 345; Found: m/z 346 (M+H)$^+$.

2 (4,3); $^1$H-NMR (D$_2$O): δ 3.00 (t, J=5.2 Hz); MALDI-TOF MS Calcd. for C$_9$H$_{19}$N$_3$O$_5$: 249; Found: m/z 250 (M+H)$^+$; Before hydrogenolysis: MALDI-TOF MS Calcd. for C$_{35}$H$_{45}$N$_3$O$_7$: 619; Found: m/z 620 (M+H)$^+$, 642 (M+Ha)$^+$.

2 (5,3); MALDI-TOF MS Calcd. for C$_{17}$H$_{29}$N$_3$O$_4$: 339; Found: m/z 340 (M+H)$^+$; Before hydrogenolysis: MALDI-TOF MS Calcd. for C$_{43}$H$_{55}$N$_3$O$_6$: 709; Found: m/z 710 (M+H)$^+$.

2 (6,3); $^1$H-NMR (D$_2$O): δ 3.54 (t, J=6.3 Hz), 3.35 (s, 3H); MALDI-TOF MS Calcd. for C$_{11}$H$_{23}$N$_3$O$_5$: 277; Found: m/z 278 (M+H)$^+$.

2 (7,3); MALDI-TOF MS Calcd. for C$_{12}$H$_{23}$N$_3$O$_5$: 289; Found: m/z 290 (M+H)$^+$; Before hydrogenolysis: MALDI-TOF MS Calcd. for C$_{38}$H$_{49}$N$_3$O$_7$: 659; Found: m/z 660 (M+H)$^+$.

2 (8,3); MALDI-TOF MS Calcd. for C$_{15}$H$_{23}$N$_3$O$_4$: 309; Found: m/z 310 (M+H)$^+$, 322 (M+Na)$^+$; Before hydrogenolysis: $^1$H-NMR (CDCl$_3$); δ 6.58, 6.46, 5.39, 5.22 (br. S, CONH$_2$); $^{13}$C-NMR (CDCl$_3$) δ 175.20 and 174.68 (CONH$_2$), 155.38 (NCOO), 28.38 (CH$_3$); MALDI-TOF MS Calcd. for C$_{41}$H$_{49}$N$_3$O$_6$: 679; Found: m/z 680 (M+H)$^+$, 2 (9,3); MALDI-TOF MS Calcd. for C$_{13}$H$_{25}$N$_3$O$_4$: 287; Found: m/z 288 (M+H)$^+$; Before hydrogenolysis: MALDI-TOF MS Calcd. for C$_{39}$H$_{51}$N$_3$O$_6$: 657: Found: m/z 658 (M+H)$^+$.

(8) Screening of Library Against Glycosidases

Incubations were performed in microtiter plate wells (50 μl/well). Reaction mixtures contained suitable buffer (40 mM phosphate buffer (pH 7) for α-glucosidase, α-galactosidase, and β-galactosidase; 20 mM acetate buffer (pH 5) for α-mannosidase; and 40 mM citrate buffer (pH 4) for α-galactosamimidase); 1 mM PNP-glycoside; given amounts of inhibitor (1 nM to 1 mM); and glycosidase (0.4 U/ml of α-glucosidase, 0.2 U/ml of α-galactosidase, 1 U/ml of β-galactosidase, 0.2 U/ml of α-mannosidase, and 0.6 U/ml of α-galactosamimidase). In the case of compound 2 (3, Y), stock 5 mM solution was first prepared by dissolving the compound in DMSO and dilution with H$_2$O(H$_2$O: DMSO=6:1 (v/v)), and aliquots of the solution was used for each reaction. After incubation at room temperature for 5 minutes, the reaction was terminated by addition of 50 μl of 0.2M sodium carbonate. Each experiment was carried in duplicate. The inhibitory results of a series of compounds in the library were shown in FIG. 6 (A to F).

(9) Assay of α-1,3-GalT-ase

Incubations were performed at pH 6.5 in the presence of α-1,3-galactosyltransferase for various time (1 to 15 minutes) for kinetic analysis. Inhibitory assays of iminosugars against α-1,3-GalT-ase were carried out under the same conditions as kinetic analysis for 5 minutes in the presence of 0.5 mM iminosugars. None of these iminosugars exhibited the inhibitory activity against α-1,3-GalT-ase.

Electrophoresis was performed at 15 kV using 60-cm fused silica capillary. The migration times for acceptor 4-MU-LacNAc (6) and product 4-MU-Gal-αl-3-Gal-β-1-4GlcNAc (7) were 9.3 minutes and 10.0 minutes, respectively. Mass spectrometric analysis of the reaction mixture after Sep-PakC18 gave satisfactory data.

MALDI-TOF MS:

Compound 6: Calcd. for C$_{24}$H$_{31}$NO$_{13}$: 541; Found: m/z 564 (M+Na)$^+$, Compound 7: Calcd. for C$_{30}$H$_{41}$NO$_{18}$: 703; Found: m/z 726 (M+Na)+

(10) Screening of Library Against β-1,4-GalT-ase

Figure 4:
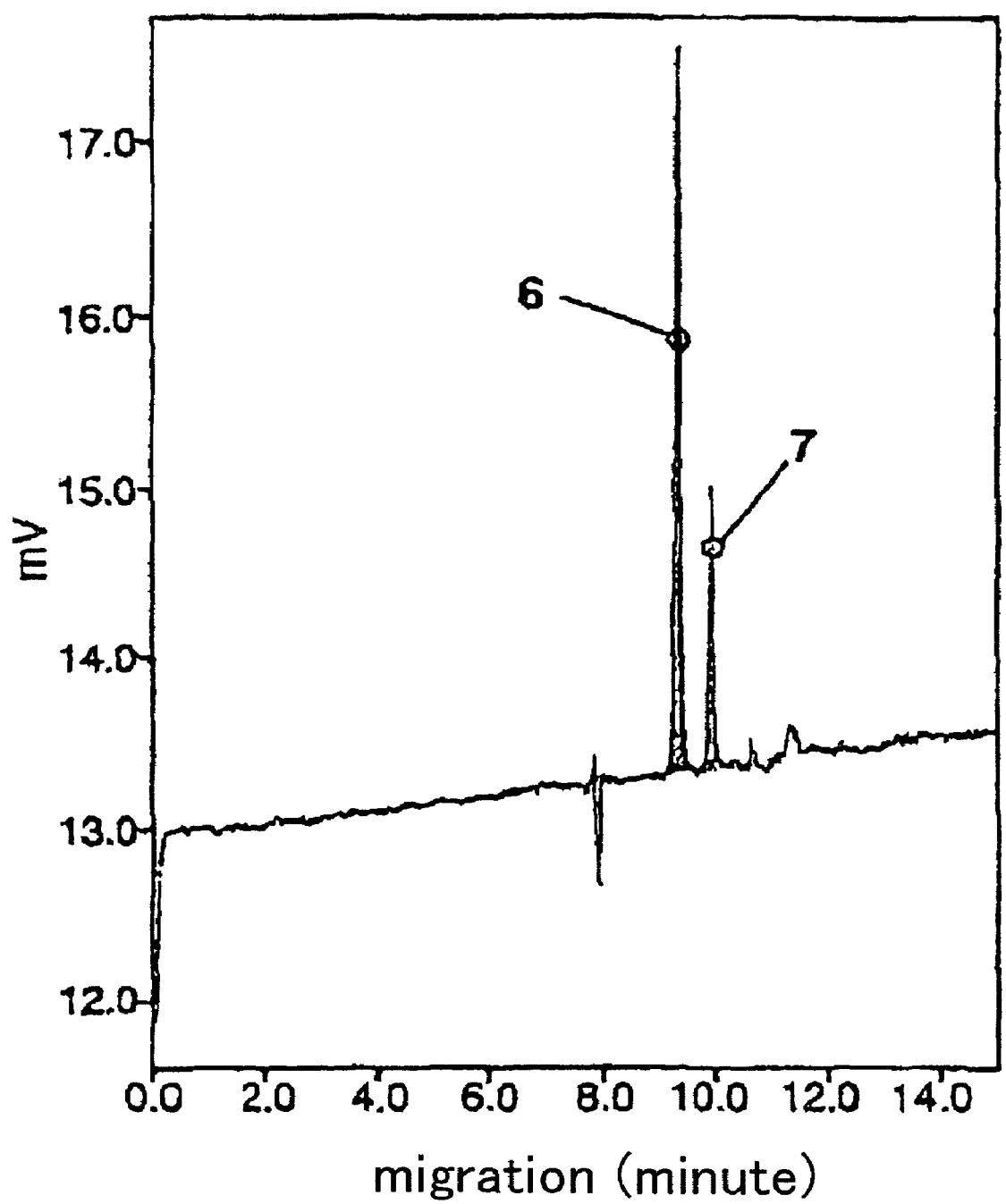
FIG. 4 shows monitoring of α-1,3-GalT-ase by capillary electrophoresis. It shows a typical electropherogram for the enzyme reactions wherein compound 6 and UDP-Gal were used as an acceptor and a donor substrate, respectively.

Incubations were performed at pH 7.0 in the presence of β-1,4-GalT-ase for various time (1 to 15 minutes) for kinetic analysis. Inhibitory assays of iminosugar were carried out under the same conditions as kinetic analysis for 5 minutes in the presence of 0.5 mM iminosugars. The inhibitory result was shown in FIG. 4(G).

Electrophoresis was performed at 20 kV using 49-cm fused silica capillary. 50 mM sodium borate was used as an electrolyte. The migration times for acceptor 4-MU-GlcNAc and product 4-MU-LacNAc (6) were 2.4 minutes and 2.6 minutes, respectively.

(B) Results and Discussions (1) Synthesis of a Combinatorial Library

Figure 1:
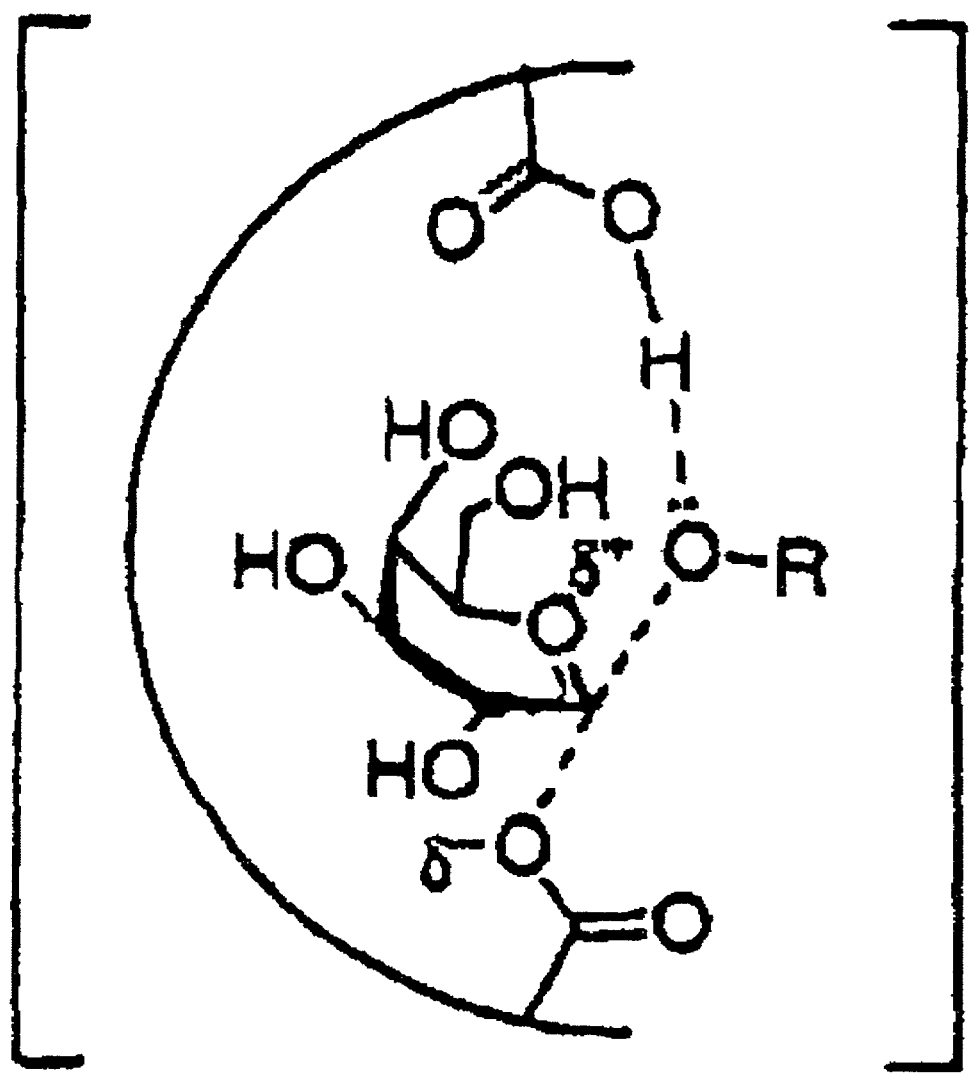
FIG. 1 shows the transition state of enzymatic hydrolysis of glycoside. Hydrolysis reaction includes the twisted half-chair conformation as a transition state.
Figure 2:
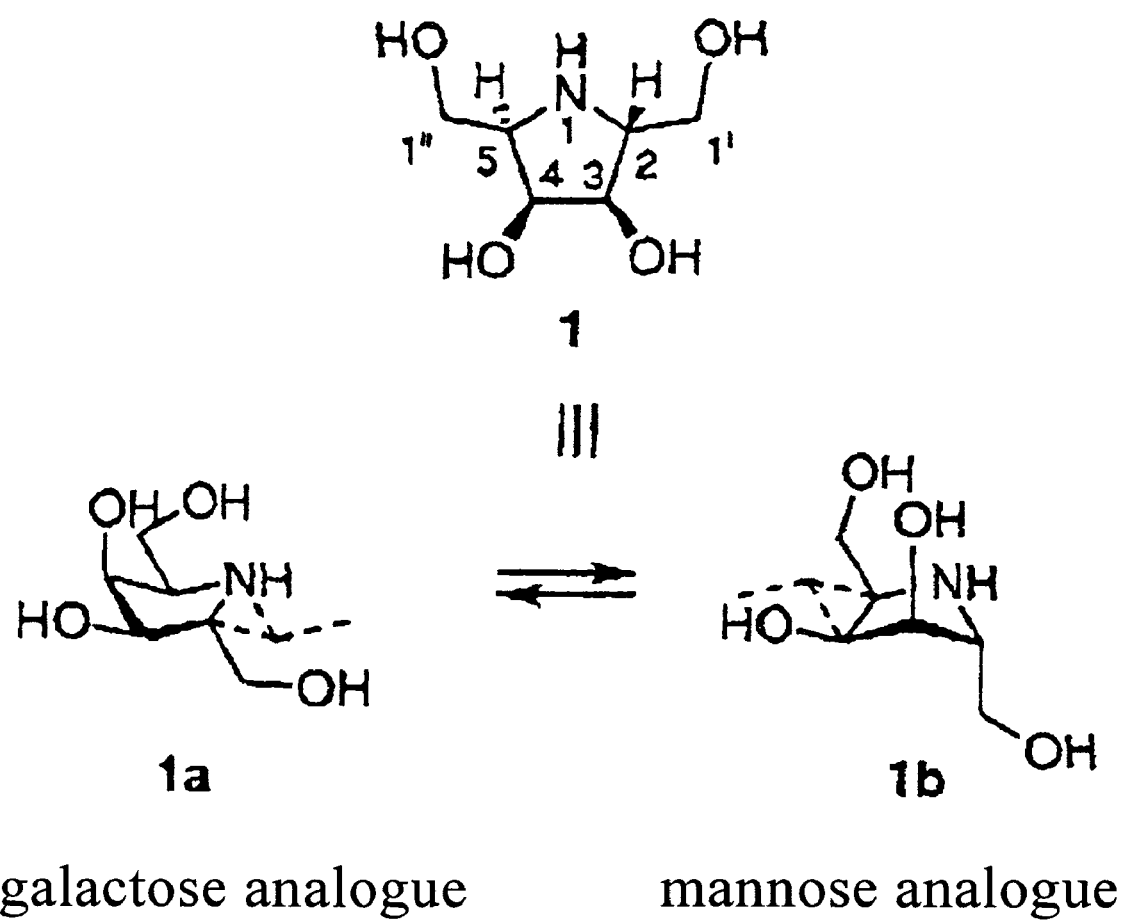
FIG. 2 shows 5-membered iminosugar 1 and two possible types of isomers. Compound 1 is a galactose or mannose analogue. An equilibration exists between isomers. Namely, "compound 1" is a candidate for a target compound against a group of different enzymes having different stereospecificity. Accordingly, 5-membered iminocyclitols are considered to have structures that are useful as the core units for designing drug molecules.
Figure 3:
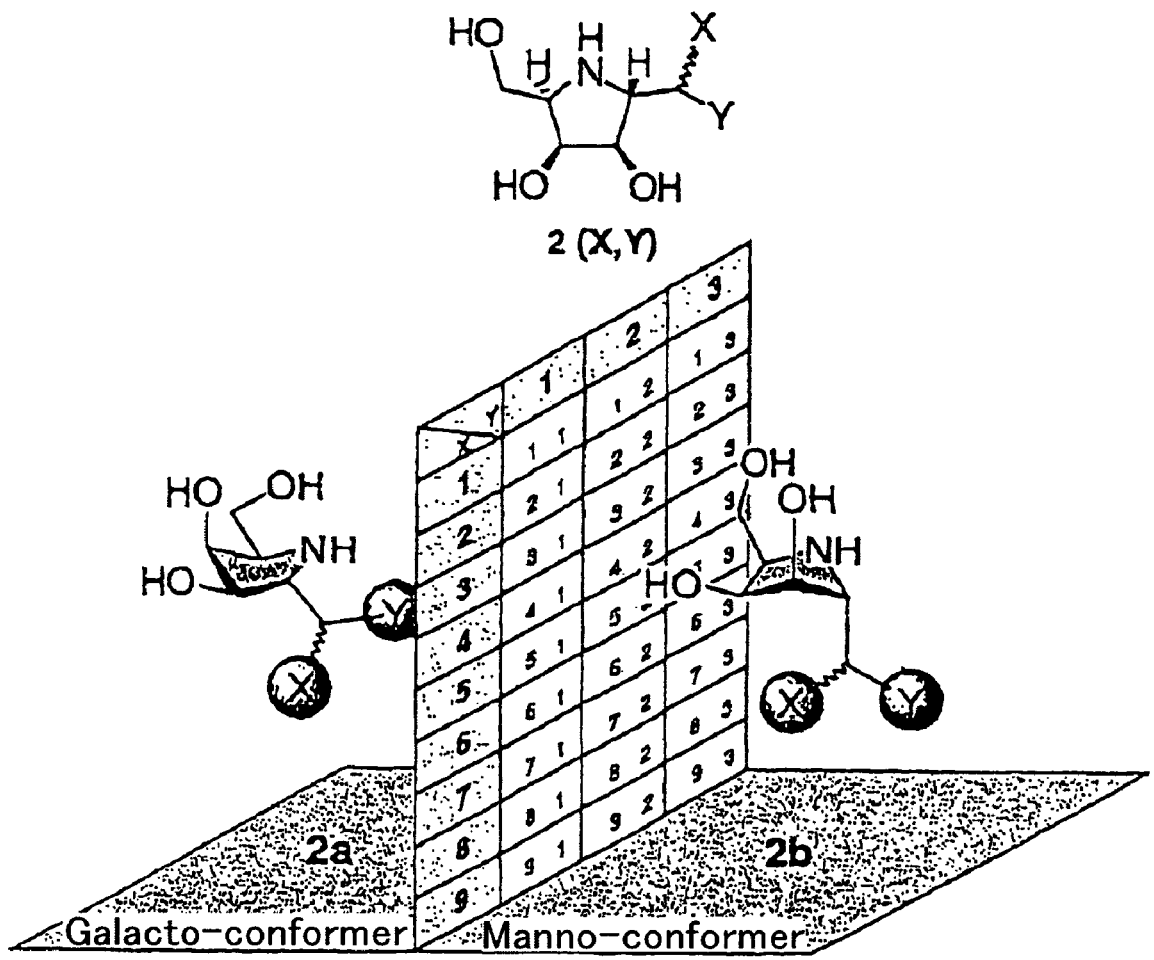
FIG. 3 shows a combinatorial library, wherein diversity is introduced at position C-1' (X, Y), and the structure thereof is shown. A group of compounds 2 (X, Y) share 5-membered iminosugar that is in an equilibrium state between the galacto isomer 2a and the manno isomer 2b.

In this example, a five-membered iminocyclitol with 2(S), 3(R), 4(S), 5(R)-configuration which is referred as either galacto-form (1a) or manno-form (1b) depending on the conformation of pyrrolidine ring, was selected (FIG. 2). Five-membered ring system is conformationally more flexible than six-membered ring system, and exists as an equilibrium of various conformers at physiological conditions. Thus, both conformers (1a and 1b) may have to be considered as structural candidates for the investigation of sugar chain related enzymes. The features of five-membered system can be considered advantageous as a lead structures for the combinatorial library, where further specificity and affinity can be drawn by the added functionalities in the structure 2. It was considered that these conformers (2a and 2b) may be treated as "conformational diversity factor" in the library because different conformers are thought to be targeted to corresponding enzyme families regarding the binding specificities (FIG. 3).

Few approaches were reported regarding carbohydrate related libraries targeting to sugar chain related enzymes (Nilsson, U. J. et al. (1998), Bioorg. Med. Chem. 6, 1563-1575; Wischnat, R. et al. (1998), Bioorg. Med. Chem. Lett. 8, 3353-3358; Lohse, A. et al. (1999), Bioorg. Med. Chem. 7, 1965-1971; Lohse, A. et al. (1999), Tetrahedron Lett. 40, 3033-3036; Takayanagi, M. et al. (2000), J. Org. Chem. 65, 3811-3815; and Malet, C. et al. (1997), Carbohydr. Res. 303, 51-65). Approaches based on the transition state inhibitors (Wischnat, R. et al. (1998), Bioorg. Med. Chem. Lett. 8, 3353-3358; Lohse, A. et al. (1999), Bioorg. Med. Chem. 7, 1965-1971; Lohse, A. et al. (1999), Tetrahedron Lett. 40, 3033-3036; and Takayanagi, M. et al. (2000), J. Org. Chem. 65, 3811-3815) are of particular interest. Several possibilities exist regarding in what way diversity is generated, namely, linear type (involves iterative reactions of doubly functionalized synthetic units), scaffold type (involves reactions of template with multiple functional groups), and cascade type (reaction product gives additional function for the next reaction) (Balkenhohl, F. et al. (1996), Angew. Chem. Int. Ed. 35, 2288-2337). Considering a series of molecules of interest have low molecular weight and should fit in the primary catalytic site of the target enzyme, which may cover approximately 100 $Å^2$ of the protein surface according to the crystallographical data of related enzymes (Murali, R. et al. (1994), J. Mol. Biol. 239, 578-580; Jacobson, R. H. et al. (1994), Nature. 369, 761-766; Gastinel, L. N. et al. (1999), EMBO J. 18, 3546-3557; Uitdehaag, J. C. M. et al. (1999), Nat. Struct. Biol. 6, 432-436; and Vallee, F. et al. (2000), EMBO. J. 19, 581-588), the added functionalities in the created molecule ($R^2$, X, and Y in the formula (I)) should not be scattered, but rather condensed close to the core unit which is an iminocyclitol.

To derive the diversity based on compound 1, the aldehyde group at C1' position was used. This was based on the observation that N-alkylation of ring nitrogen is often resulted in decreased inhibitory at molecular level (Takebayashi, M. et al. (1999), J. Org. Chem. 64, 5280-5291; and Saotome, C. et al. (2000), Bioorg. Med. Chem. 8, 2249-2261), although increased hydrophobicity is advantageous to penetrate cell membrane (Fleet, G. W. J. et al. (1988), FEBS Lett. 237, 128-132; Karpas, A. et al. (1988), Proc. Natl. Acad. Sci. USA. 85, 9229-9233; and Asano, N. et al. (1995), J. Med. Chem. 38, 2349-2356). Aldehyde 3 was synthesized as reported above, and used to create a library (Saotome, C. et al. (2000), Bioorg. Med. Chem. 8, 2249-2261). First, imine formed by reaction of compound 3 and amines was utilized for various reaction conditions including reductive amination, Strecker condensation, Ugi-type reaction and Mannich reaction, and polyethylene glycol (PEG) was introduced by acylation of the product to enhance the diversity, thereby facilitating the "fish-out" proces of the condensation product from a reaction mixture. However, it was found that some of the reactions did not give satisfactory results. It was suggested this was caused due to severe steric problems of t-butylcarbonyl (Boc), benzyl (Bn), and X of amines around the reaction site. Reactions, which were found applicable, were reductive amination and Strecker reaction without following acylation, but the applicable reactions are not limited thereto, and other reactions may be employed as long as a desirable product can be obtained. Large diversity could not be obtained in iminocyclitol-based library, but alternatively, transformation reactions of a nitrile group into amino, amide and carboxylic acid (Ys) were included. The selected groups X and Y are shown in FIG. 3.

At first, reductive amination reactions of compound 3 using variety of amines (X—H) were carried out. Reduction of imine proceeded smoothly under standard condition with sodium cyanoborohydride to give compounds 4 (1-9), which were deprotected in one-step by hydrogenolysis under acidic condition to afford compound 2 (1-9, 1) in good yields using Sep-Pak CM cartridge. Individual conversion rate of reductive amination reaction was estimated by densitographical analysis of TLC plate, which indicated that compound 3 was transformed into compound 4 in a range of 42 to 98% yield.

Next, the Strecker reaction was carried out. Trimethylsilylcyanide (TMSCN) was used in the presence of catalytic $ZnCl_2$ after imine formation with 9 amines (Ojima, I. et al. (1975), Chem. Lett. 737-740) (Scheme 1, FIG. 3). It was found that the reactions did not proceed without Lewis acid. No significant stereoselectivity was observed in any case, which suggested that Lewis acid directly activated the imine intermediate but not through other functional groups since auxiliary effect could not be observed. The condensation products were subjected to the following reactions without isolation. The conversion rate of the aldehyde 3 into compound 5 was in a range of 57 to 97% according to densitography. The mixtures were subjected to various reaction conditions such as hydrolysis and reduction to transfer nitrile group into carboxylate, amide and amine respectively. Reduction of Compound 5 (1-9) to convert into amine 2 (1-9, 2) was achieved under acidic hydrogenolysis condition, which removed Boc and Bn groups at the same time. When it was attempted to hydrolyze the nitrile group to obtain carboxylic acid and amide (Y), both acidic and basic hydrolytic conditions gave complex mixtures. Thus, compound 5 (1-9) were converted oxidatively into amides, which were then hydrogenolyzed to compound 2 (1-9, 3). Further transformation of the intermediate to carboxylate under the condition even after raising the temperature failed.

Scheme 1:

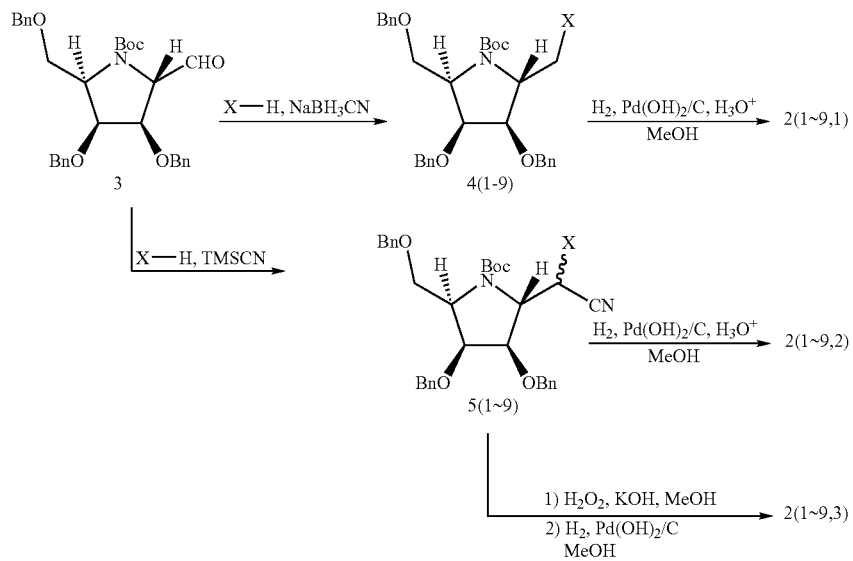

Synthesis of a Library of Compound 2 (X, Y):

Compounds 4 (X) and 5 (Y) were formed by reductive amination and the Strecker reaction of aldehyde 3. The nitrile group in compound 5 (X) was further converted into an amine- and amide-functional groups of Y. These compounds were deprotected to obtain compound 2 (X, Y).

Compound 2 (1-9, 1) was used as a candidate of inhibitors, and sugar chain related enzymes to be tested were selected. α-Gal-ase, β-Gal-ase, and α-GalNAc-ase were chosen as the counter part of galacto-conformer compound 2a (X, Y) (FIG. 3). Two glycosyltransferases, namely β-1, 4-GalT-ase and α-1,3-GalT-ase, were also included because compound 1 was inhibitor of β-1,4-GalT-ase against UDP-Gal with K1 value of 27 μM (Saotome, C. et al. (2000), Bioorg. Med. Chem. 8, 2249-2261). In the same manner, α-Man-ase was selected for manno-conformer compound 2b (X, Y). α-Glc-ase was also added.

(2) Screening of the Library Against Sugar Chain Related Enzymes

Figure 5:
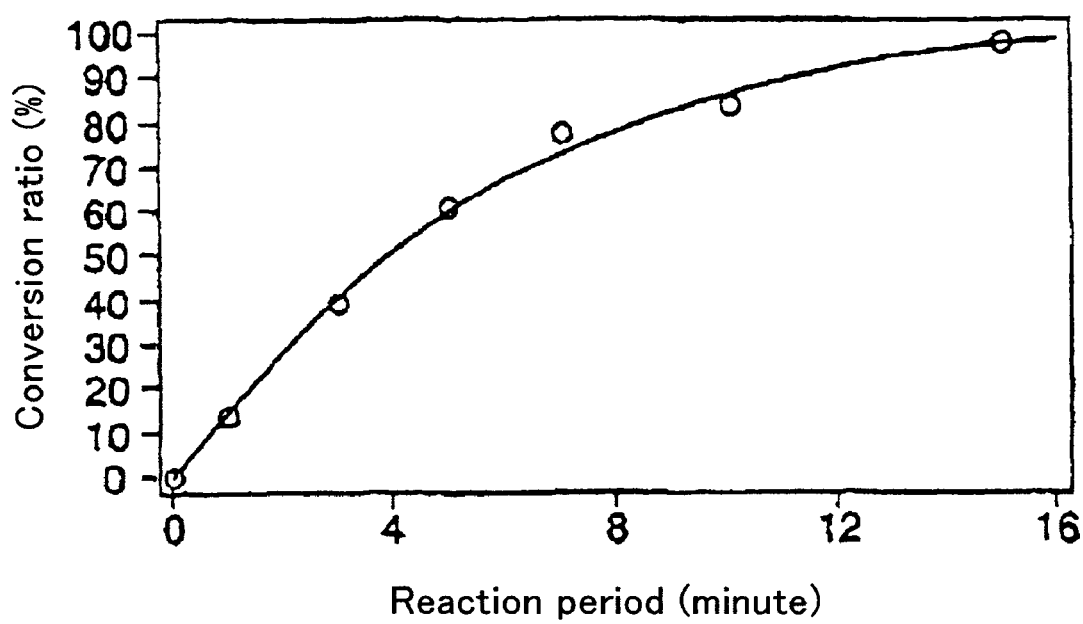
FIG. 5 shows the time course during the α-1,3-GalT-ase reaction. α-Galactosyl transition was examined with the time course. The reaction was completed in 16 minutes.

In order to assay inhibitory effects of the library compounds against α-1,3-galactosyltransferase (Sharma, A. et al. (1996), Proc. Natl. Acad. Sci. USA. 93, 7190-7195; Sujino, K. et al. (1998), Carbohydr. Res. 305, 483-489; Chen, X. et al. (1999), Curr. Opin. Chem. Biol. 3, 650-658; and Takayama, S. et al. (1999), Bioorg. Med. Chem. 7, 401-409), the required substrate and the product were synthesized first using the enzyme. 4-Methylumbelliferyl(4-MU) LacNAc (compound 6) was synthesized according to the previously reported method (Kanie, Y. et al. (1998), Anal. Biochem. 263, 240-245), and was used as the substrate. Formation of compound 7 during the reaction of compound 6 and UDP-Gal in the presence of a transferase was confirmed by using capillary electrophoresis as typical electropherogram shown in FIG. 4 (Scheme 2). The time course study of the enzyme reaction was also carried out (FIG. 5). Under the condition, the transfer reaction completed after 16 minutes. Although compound 7 was not isolated, MALDI-TOF mass spectral analysis of the reaction mixture after Sep-Pak C18 showed presence of compounds 6 and 7.

Scheme 2:

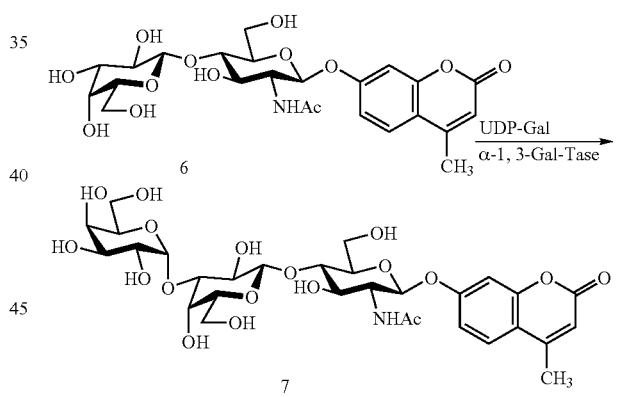

Synthesis of Xeno-tri-carbohydrate:

4-MU-LacNAc (6) prepared from 4-MU-GlcNAc was converted into a xenoantigenic tri-carbohydrate in the presence of UDP-Gal utilizing the action of α-1,3-galactosyl-transferase.

To examine potentials of the method according to the present invention and to inspect whether or not each member of the library can be inhibitors of glucosidase and glycosyltransferase, preliminary inhibition screening assay was carried out at fixed concentration of potential inhibitors. The suitable concentration in each enzyme reaction was determined by initial inhibitory test using a compound in a library and/or known inhibitors of the enzyme at various concentrations. Inhibitory was shown in percentage at the concentration determined. Each enzyme reaction was performed in a well of a titer plate and the inhibitory against corresponding substrates was estimated by absorbance at 405 nm for p-nitrophenol in the case of assays of glycosidases. Common inhibitors were used for the generality of the result when they are available.

For the inhibition assays of glycosyltransferase, corresponding 4-MU-glycosides such as 4-MU-GlcNAc, compound 6 and compound 7, were used. Inhibition reactions were carried out in microcentrifuge tubes for 5 minutes, and the inhibitory activities were determined as conversion rate relative to the acceptor substrate using capillary electrophoresis at 214 nm.

Figure 6:
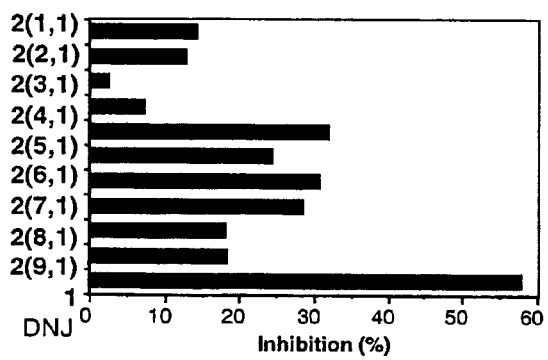
FIG. 6 shows inhibitory activities of compound 2 (S, 1) against various sugar chain related enzymes.
Figure 6:
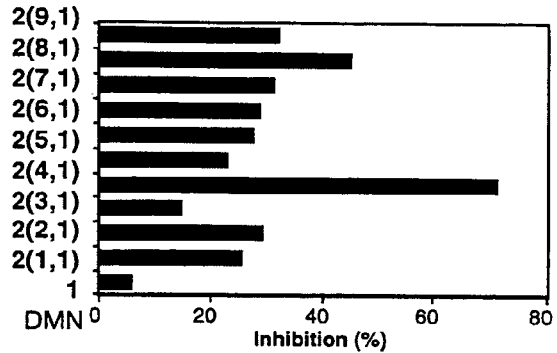
Figure 6:
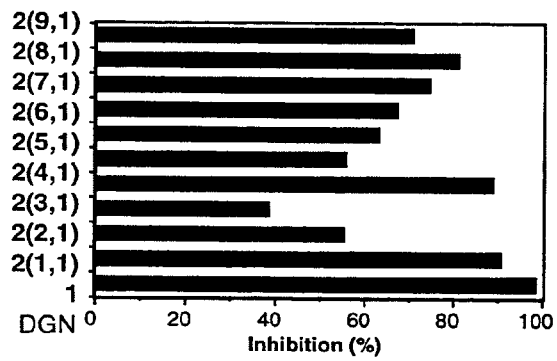
Figure 6:
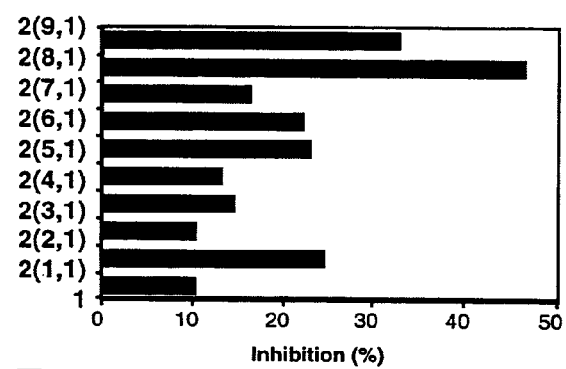
Figure 6:
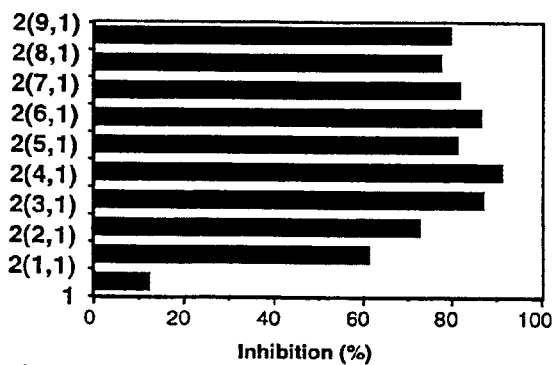
Figure 6:
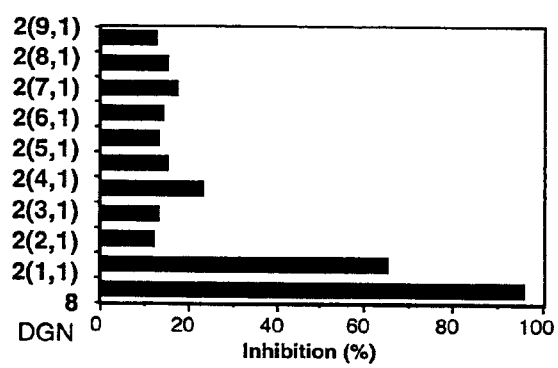
Figure 6:
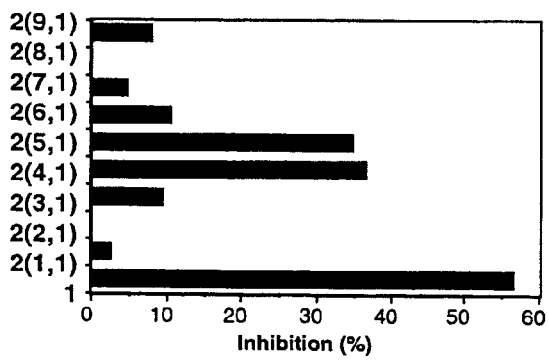
Figure 6:
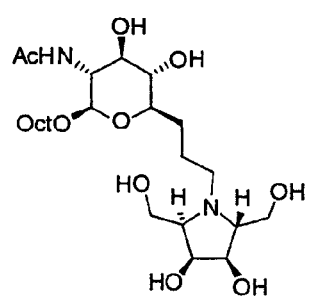

As shown in FIG. 6, a series of compounds in the library showed broad inhibitory spectra for the enzymes tested, except for α-1,3-GalT-ase of which graph was omitted since no inhibition was observed. Depending on the enzyme, some compounds showed dramatic enhancement of inhibition activities compared to the parent compound 1. Such examples was found for α-Glc-ase (A), α-Man-ase (B), α-Gal-ase (C), α-GalNAc-ase (D), and β-Gal-ase (E, F). For the inhibition of α-Glc-ase with inhibitor concentration at 100 μM, some were found to have as twice as potent as compound 1, although none showed comparable inhibitory to deoxynojirimycin (DNJ). It was found that hydrophobicity far from iminosugar is preferred in the case of α-Man-ase, where compound 2 (3, 1) with $C_{10}$-alkyl group showed 276% and 1120% enhancement of inhibitory at 10 μM concentration against compound 1 (Ki=27 μM) (Saotome, C. et al. (2000), Bioorg. Med. Chem. 8, 2249-2261) and deoxymannojirimycin (DMN, Ki=43 μM) (Saotome, C. et al. (2000), Bioorg. Med. Chem. 8, 2249-2261), respectively. For the inhibition of α-GalNAc-ase, only Siastatin B analog is reported as inhibitor with $IC_{50}$ value of μM range (Nishimura Y. et al. (1996), Bioorg. Med. Chem. 4, 91-96). Five of eight compounds were found more than twice as potent compared to their parent compound (1) at nM order. Among them, compound 2 (8, 1) having phenethyl group showed 467% stronger activity. In the case of β-Gal-ase, all the compounds tested were found much better inhibitors of the enzyme compared to compound 1 (Ki=1.0 mM) (Saotome, C. et al. (2000), Bioorg. Med. Chem. 8, 2249-2261), however, they only exhibited weak inhibitory at μM range as shown in (F). Also, it was suggested that the substitution at C-1' position was not important for the binding since there was no significant difference in activities among the compounds. It is worth noting that some compounds were inhibitory against β-GalT-ase despite none inhibited α-GalT-ase even two enzymes, β-GalT-ase (G) and α-GalT-ase share UDP-Gal as donor substrates, and the compound according to the present invention can mimic donor transition state.

Compounds shown to have strong inhibitory effects such as compounds 2 (3, 1) and 2 (8, 1) were selected as lead compounds for further evaluations to see the effects of Y group (FIG. 7). Compounds 2 (3, 2) and 2 (3, 3) lost almost all inhibitory activity against α-Man-ase at the concentration. Compounds 2 (8, 2) and 2 (8, 3) inhibited α-GalNAc-ase at the condition with 52.8% and 50.5% of inhibitory effect of compound 2 (8, 1), respectively.

Completely different inhibition spectra were observed for enzymes tested, which indicates that the selectivity can be controlled by a substituent groups at C-1' position with keeping the core unit the same. In addition, these compounds showed inhibitory against enzymes of which substrate specificities are against both galacto- and manno-series. This observation suggests that the library of pyrrolidine rings can be treated as mixtures having different conformations, and thus, the compound of the present invention is very useful.

INDUSTRIAL APPLICABILITY

The present invention provides a novel azasugar compound. The azasugar compound of the present invention is useful as a specific inhibitor of sugar chain related enzymes such as glycosyltransferase and glycosidase. For example, this compound is useful as medicine for treating or preventing diseases associated with sugar chain related enzymes, and more specifically it is useful as an antiviral agent, an anticancer agent, or an immunostimulant agent.

Numerous difficulties remain concerning the effective design and synthesis of sugar chain related enzymes. However, a method of synthesizing a combinatorial library has drawn the attention of those involved in the development of pharmaceuticals as an effective means for rapidly finding highly active compounds in combination with high throughput screening. In contrast, a novel enzyme inhibitor can be discovered by focusing on induced-fit-based recognition by conformational rearrangement of peptide chains in the enzyme. Induced fit is classified into two cases where an enzyme varies its structure and where a substrate or inhibitor varies its structure to be compatible with the structure of the active site of the enzyme. A five-membered cyclic compound not only imitates the half-chair-type conformation of the transition state, but also the ring structure has a wide range of freedom. A five-membered cyclic azasugar having a hydroxyl group of specific configuration can imitate a different sugar through conformational changes. Namely, a five-membered azasugar can select a more adequate conformation for an enzyme given by the induced fit. Therefore, the compounds of the present invention can be provided as a compound library with utility values generated by conformational diversity, and is useful for developing pharmaceuticals.

The invention claimed is:

1. A compound represented by the following formula (Ia) or a salt thereof:

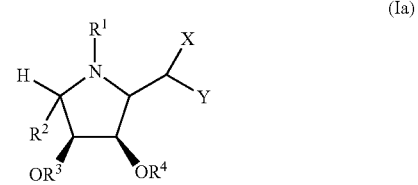

(Ia)

wherein $R^1$ represents a hydrogen atom, a $C_{1-10}$ alkyl group optionally having a substituent, or a protecting group of N; $R^2$ represents a $C_{1-10}$ alkyl group optionally having a substituent or a $C_{2-10}$ alkenyl group optionally having a substituent; $R^3$ and $R^4$ independently represent a hydrogen atom or a protecting group of hydroxyl group; X represents —N($R^5$)$R^6$ or a residue of amino acid or of an amino group of a peptide wherein $R^5$ and $R^6$ independently represent a hydrogen atom, a $C_{1-10}$ alkyl group optionally having a substituent, or a $C_{3-12}$ cycloalkyl group optionally having a substituent; and Y represents a hydrogen atom, —$CH_2NH_2$, —$CONH_2$, or —COOH.

2. The compound according to claim 1 or a salt thereof, wherein the configuration of the formula (Ia) is represented by the following formula (Ib):

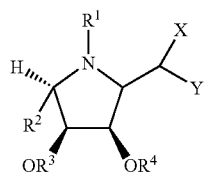

wherein $R^1$, $R^2$, $R^3$, $R^4$, X, and Y are as defined in claim 1.

3. The compound according to claim 1 or a salt thereof, wherein the configuration of the formula (Ia) is represented by the following formula (Ic):

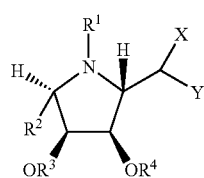

wherein $R^1$, $R^2$, $R^3$, $R^4$, X, and Y are as defined in claim 1.

4. The compound according to claim 1 or a salt thereof, wherein $R^2$ represents —$CH_2OR^{12}$ wherein $R^{12}$ represents a hydrogen atom or a protecting group of hydroxyl group.

5. An inhibitor composition of sugar chain related enzymes which comprises, as an active ingredient, the compound of claim 1 or a salt thereof.

6. A pharmaceutical composition which comprises, as an active ingredient, the compound of claim 1 or a salt thereof.

7. The pharmaceutical composition according to claim 6 which is an antiviral agent, an anticancer agent, or an immunostimulant agent.

8. The compound according to claim 2 or a salt thereof, wherein $R^2$ represents —$CH_2OR^{12}$ wherein $R^{12}$ represents a hydrogen atom or a protecting group of hydroxyl group.

9. The compound according to claim 3 or a salt thereof, wherein $R^2$ represents —$CH_2OR^{12}$ wherein $R^{12}$ represents a hydrogen atom or a protecting group of hydroxyl group.

10. A method of treating diseases associated with sugar chain related enzymes comprising administering a therapeutically effective amount of the compound according to claim 1 or a salt thereof to a mammal.

11. A method of treating diseases associated with sugar chain related enzymes comprising administering a therapeutically effective amount of the compound according to claim 2 or a salt thereof to a mammal.

12. A method of treating diseases associated with sugar chain related enzymes comprising administering a therapeutically effective amount of the compound according to claim 3 or a salt thereof to a mammal.

13. A method of administering an antiviral agent, an anticancer agent, or an immunostimulant agent to a mammal comprising administering a compound according to claim 1 or a salt thereof to the mammal.

14. A method of administering an antiviral agent, an anticancer agent, or an immunostimulant agent to a mammal comprising administering a compound according to claim 2 or a salt thereof to the mammal.

15. A method of administering an antiviral agent, an anticancer agent, or an immunostimulant agent to a mammal comprising administering a compound according to claim 3 or a salt thereof to the mammal.

16. The method according to claim 10 wherein the mammal is a human.

17. The method according to claim 11 wherein the mammal is a human.

* * * * *